(12) United States Patent
Burnett et al.

(10) Patent No.: US 9,005,102 B2
(45) Date of Patent: *Apr. 14, 2015

(54) METHOD AND APPARATUS FOR ELECTRICAL STIMULATION THERAPY

(75) Inventors: Daniel R. Burnett, San Francisco, CA (US); Christopher Hermanson, Santa Cruz, CA (US); James H. Ahlman, Sunnyvale, CA (US); Bruno Strul, Portola Valley, CA (US)

(73) Assignee: EMKinetics, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/457,228

(22) Filed: Apr. 26, 2012

(65) Prior Publication Data
US 2013/0072746 A1    Mar. 21, 2013

Related U.S. Application Data

(63) Continuation of application No. PCT/US2010/054353, filed on Oct. 27, 2010, which is a continuation-in-part of application No. 12/606,941, filed on Oct. 27, 2009, now abandoned, which is a (Continued)

(51) Int. Cl.
*A61N 1/36* (2006.01)
*A61N 2/00* (2006.01)
(Continued)

(52) U.S. Cl.
CPC .... *A61N 2/006* (2013.01); *A61N 2/02* (2013.01); *A61N 1/36007* (2013.01); *A61N 1/36014* (2013.01); *A61N 1/08* (2013.01); *A61N 2/004* (2013.01)

(58) Field of Classification Search
USPC ............... 600/9–15; 607/2–76, 115–156; 601/15–22; 606/32–52
See application file for complete search history.

(56) References Cited

U.S. PATENT DOCUMENTS 2,893,392 A    7/1959  Wagner et al.
3,034,507 A    5/1962  McConnell et al.
(Continued)

FOREIGN PATENT DOCUMENTS

GB    0637560    5/1950
GB    2298370    9/1996
(Continued)

OTHER PUBLICATIONS

McGuire EJ et al. Treatment of motor and sensory detrusor instability by electrical stimulation. The Journal of Urology 129(1); p. 78-79, 1983.*

(Continued)

*Primary Examiner* — Catherine B Kuhlman
(74) *Attorney, Agent, or Firm* — Levine Bagade Han LLP

(57) ABSTRACT

Energy emitting systems are provided which include an adjustable conductive coil configured to generate a magnetic or electromagnetic field focused on a target nerve. The coil includes a central aperture which may be adjustable between a first configuration and a second configuration having a radius greater than the radius of the first configuration. The adjustable or movable nature of the coil allows the conductive coil to conform to, accommodate, or be positioned on a particular anatomical structure of a patient to position the coil in proximity to the underlying target nerve. In certain embodiments, methods of magnetic induction therapy are provided which include positioning a conductive coil relative to a portion of a patient's body by adjusting the central aperture of the coil such that the coil may conform to, accommodate or be positioned on the portion of the patient's body in proximity to the underlying target nerve.

5 Claims, 17 Drawing Sheets

Related U.S. Application Data continuation-in-part of application No. 11/866,329, filed on Oct. 2, 2007.

(60) Provisional application No. 60/848,720, filed on Oct. 2, 2006.

(51) Int. Cl.
*A61N 2/02* (2006.01)
*A61N 1/08* (2006.01)

(56) References Cited

U.S. PATENT DOCUMENTS

| | | |
|---|---|---|
| 3,817,254 A | 6/1974 | Maurer |
| 3,841,305 A | 10/1974 | Hallgren |
| 4,233,965 A | 11/1980 | Fairbanks |
| 4,266,533 A | 5/1981 | Ryaby et al. |
| 4,428,366 A | 1/1984 | Findl et al. |
| 4,456,012 A | 6/1984 | Lattin |
| 4,548,208 A | 10/1985 | Niemi |
| 4,574,809 A | 3/1986 | Talish et al. |
| 4,784,737 A | 11/1988 | Ray et al. |
| 4,804,054 A | 2/1989 | Howson et al. |
| 4,837,049 A * | 6/1989 | Byers et al. ............ 216/6 |
| 4,915,110 A | 4/1990 | Kitov |
| 4,926,878 A | 5/1990 | Snedeker |
| 4,940,453 A | 7/1990 | Cadwell |
| 5,000,178 A | 3/1991 | Griffith |
| 5,014,699 A | 5/1991 | Pollack et al. |
| 5,092,835 A | 3/1992 | Schurig et al. |
| 5,158,080 A | 10/1992 | Kallok |
| 5,181,902 A | 1/1993 | Erickson et al. |
| 5,309,909 A | 5/1994 | Gadsby et al. |
| 5,314,401 A | 5/1994 | Tepper |
| 5,314,453 A | 5/1994 | Jeutter |
| 5,401,233 A | 3/1995 | Erickson et al. |
| 5,449,378 A | 9/1995 | Schouenborg |
| 5,518,495 A | 5/1996 | Kolt |
| 5,562,707 A | 10/1996 | Prochazka et al. |
| 5,690,693 A | 11/1997 | Wang et al. |
| 5,715,837 A | 2/1998 | Chen |
| 5,725,471 A | 3/1998 | Davey et al. |
| 5,749,909 A | 5/1998 | Schroeppel et al. |
| 5,766,124 A | 6/1998 | Polson |
| 5,792,187 A | 8/1998 | Adams |
| 5,792,209 A | 8/1998 | Varner |
| 5,833,600 A | 11/1998 | Young |
| 5,857,957 A | 1/1999 | Lin |
| 5,978,712 A | 11/1999 | Suda et al. |
| 5,984,854 A | 11/1999 | Ishikawa et al. |
| 6,009,878 A | 1/2000 | Weijand et al. |
| 6,024,691 A | 2/2000 | Tepper et al. |
| 6,029,090 A | 2/2000 | Herbst |
| 6,032,677 A | 3/2000 | Blechman et al. |
| 6,066,084 A | 5/2000 | Edrich et al. |
| 6,086,525 A | 7/2000 | Davey et al. |
| 6,088,619 A | 7/2000 | Hein et al. |
| 6,123,658 A | 9/2000 | Schweighofer et al. |
| 6,143,035 A | 11/2000 | McDowell |
| 6,155,966 A | 12/2000 | Parker |
| 6,179,770 B1 | 1/2001 | Mould |
| 6,190,893 B1 | 2/2001 | Shastri et al. |
| 6,200,259 B1 | 3/2001 | March |
| 6,213,933 B1 | 4/2001 | Lin |
| 6,219,575 B1 | 4/2001 | Nemati |
| 6,256,533 B1 | 7/2001 | Yuzhakov et al. |
| 6,261,221 B1 | 7/2001 | Tepper et al. |
| 6,312,612 B1 | 11/2001 | Sherman et al. |
| 6,319,241 B1 * | 11/2001 | King et al. ............ 604/502 |
| 6,334,856 B1 | 1/2002 | Allen et al. |
| 6,349,233 B1 | 2/2002 | Adams |
| 6,366,795 B1 | 4/2002 | Bremer et al. |
| 6,379,324 B1 | 4/2002 | Gartstein et al. |
| 6,440,096 B1 | 8/2002 | Lastovich et al. |
| 6,443,883 B1 | 9/2002 | Ostrow et al. |
| 6,451,240 B1 | 9/2002 | Sherman et al. |
| 6,471,903 B2 | 10/2002 | Sherman et al. |
| 6,473,652 B1 | 10/2002 | Sarwal et al. |
| 6,491,620 B1 | 12/2002 | Davey |
| 6,493,588 B1 | 12/2002 | Malaney et al. |
| 6,500,110 B1 | 12/2002 | Davey et al. |
| 6,503,231 B1 | 1/2003 | Prausnitz et al. |
| 6,511,463 B1 | 1/2003 | Wood et al. |
| 6,527,694 B1 | 3/2003 | Ishikawa et al. |
| 6,533,949 B1 | 3/2003 | Yeshurun et al. |
| 6,537,242 B1 | 3/2003 | Palmer |
| 6,553,263 B1 | 4/2003 | Meadows et al. |
| 6,558,361 B1 | 5/2003 | Yeshurun |
| 6,565,532 B1 | 5/2003 | Yuzhakov et al. |
| 6,582,393 B2 | 6/2003 | Sage, Jr. |
| 6,591,124 B2 | 7/2003 | Sherman et al. |
| 6,595,947 B1 | 7/2003 | Mikszta et al. |
| 6,603,987 B2 | 8/2003 | Whitson |
| 6,611,707 B1 | 8/2003 | Prausnitz et al. |
| 6,622,035 B1 | 9/2003 | Merilainen et al. |
| 6,623,457 B1 | 9/2003 | Rosenberg |
| 6,652,443 B1 | 11/2003 | Struppler et al. |
| 6,652,478 B1 | 11/2003 | Gartstein et al. |
| 6,654,636 B1 | 11/2003 | Dev et al. |
| 6,656,147 B1 | 12/2003 | Wilkinson et al. |
| 6,663,556 B2 | 12/2003 | Barker |
| 6,663,820 B2 | 12/2003 | Arias et al. |
| 6,671,527 B2 | 12/2003 | Petersson et al. |
| 6,678,556 B1 | 1/2004 | Nolan et al. |
| 6,684,106 B2 | 1/2004 | Herbst |
| 6,689,100 B2 | 2/2004 | Connelly et al. |
| 6,690,959 B2 | 2/2004 | Thompson |
| 6,697,669 B2 | 2/2004 | Dev et al. |
| 6,701,185 B2 | 3/2004 | Burnett et al. |
| 6,735,474 B1 | 5/2004 | Loeb et al. |
| 6,743,211 B1 | 6/2004 | Prausnitz et al. |
| 6,767,341 B2 | 7/2004 | Cho |
| 6,770,022 B2 | 8/2004 | Mechlenburg et al. |
| 6,770,480 B1 | 8/2004 | Canham |
| 6,782,283 B2 | 8/2004 | Schmidt et al. |
| 6,790,372 B2 | 9/2004 | Roy et al. |
| 6,808,506 B2 | 10/2004 | Lastovich et al. |
| 6,835,184 B1 | 12/2004 | Sage et al. |
| 6,866,659 B2 | 3/2005 | Nemati |
| 6,881,203 B2 | 4/2005 | Delmore et al. |
| 6,899,838 B2 | 5/2005 | Lastovich |
| 6,908,453 B2 | 6/2005 | Fleming et al. |
| 6,926,660 B2 | 8/2005 | Miller |
| 6,931,277 B1 | 8/2005 | Yuzhakov et al. |
| 6,939,311 B2 | 9/2005 | Geiger |
| 6,941,171 B2 | 9/2005 | Mann et al. |
| 6,960,193 B2 | 11/2005 | Rosenberg |
| 6,962,772 B2 | 11/2005 | Liu et al. |
| 6,972,013 B1 | 12/2005 | Zhang et al. |
| 6,980,855 B2 | 12/2005 | Cho |
| 7,013,179 B2 | 3/2006 | Carter et al. |
| 7,027,478 B2 | 4/2006 | Ackley |
| 7,032,302 B1 | 4/2006 | Schmidt et al. |
| 7,045,069 B2 | 5/2006 | Ozeryansky |
| 7,047,070 B2 | 5/2006 | Wilkinson et al. |
| 7,048,723 B1 | 5/2006 | Frazier et al. |
| 7,079,355 B2 | 7/2006 | Hsiao et al. |
| 7,083,592 B2 | 8/2006 | Lastovich et al. |
| 7,104,947 B2 | 9/2006 | Riehl |
| 7,115,108 B2 | 10/2006 | Wilkinson et al. |
| 7,117,034 B2 | 10/2006 | Kronberg |
| 7,130,696 B2 | 10/2006 | Carter et al. |
| 7,132,054 B1 | 11/2006 | Kravitz et al. |
| 7,153,256 B2 | 12/2006 | Riehl et al. |
| 7,187,976 B2 | 3/2007 | Duncan et al. |
| 7,226,439 B2 | 6/2007 | Prausnitz et al. |
| 7,262,068 B2 | 8/2007 | Roy et al. |
| 7,273,474 B2 | 9/2007 | Chang et al. |
| 7,285,113 B2 | 10/2007 | Yeshurun |
| 7,315,758 B2 | 1/2008 | Kwiatkowski et al. |
| 7,316,665 B2 | 1/2008 | Laurent et al. |
| 7,320,664 B2 | 1/2008 | Riehl et al. |
| 7,332,197 B2 | 2/2008 | Wood et al. |
| 7,332,339 B2 | 2/2008 | Canham |

(56) References Cited

U.S. PATENT DOCUMENTS

| | | | |
|---|---|---|---|
| 7,344,499 | B1 | 3/2008 | Prausnitz et al. |
| 7,367,936 | B2 | 5/2008 | Myers et al. |
| D571,920 | S | 6/2008 | Juliana et al. |
| 7,396,326 | B2 | 7/2008 | Ghiron et al. |
| 7,410,476 | B2 | 8/2008 | Wilkinson et al. |
| 7,415,299 | B2 | 8/2008 | Zimmermann et al. |
| 7,416,541 | B2 | 8/2008 | Yuzhakov et al. |
| 7,429,333 | B2 | 9/2008 | Chiou et al. |
| 7,473,244 | B2 | 1/2009 | Frazier et al. |
| 7,481,337 | B2 | 1/2009 | Luharuka et al. |
| 7,497,980 | B2 | 3/2009 | Xu et al. |
| 7,500,911 | B2 | 3/2009 | Johnson et al. |
| 7,520,848 | B2 | 4/2009 | Schneider et al. |
| 7,522,061 | B2 | 4/2009 | Rondoni et al. |
| 7,530,968 | B2 | 5/2009 | Gonnelli |
| 7,536,226 | B2 | 5/2009 | Williams et al. |
| 7,556,615 | B2 | 7/2009 | Pettis et al. |
| 7,556,821 | B2 | 7/2009 | Ameri et al. |
| 7,560,036 | B2 | 7/2009 | Golubovic-Liakopoulos et al. |
| 7,570,992 | B2 | 8/2009 | Nolan et al. |
| 7,572,405 | B2 | 8/2009 | Sherman et al. |
| 7,574,256 | B2 | 8/2009 | Carter |
| 7,578,954 | B2 | 8/2009 | Gartstein et al. |
| 7,582,069 | B2 | 9/2009 | Laurent et al. |
| 7,588,552 | B2 | 9/2009 | Yeshurun et al. |
| 7,591,806 | B2 | 9/2009 | Xu |
| 7,627,938 | B2 | 12/2009 | Kim et al. |
| 7,647,112 | B2 | 1/2010 | Tracey et al. |
| 7,648,484 | B2 | 1/2010 | Yeshurun et al. |
| 7,651,946 | B2 | 1/2010 | Wilke et al. |
| 7,658,728 | B2 | 2/2010 | Yuzhakov |
| 7,941,201 | B2 | 5/2011 | Chiou et al. |
| 8,430,805 | B2 | 4/2013 | Burnett et al. |
| 2002/0028991 | A1 | 3/2002 | Thompson |
| 2002/0082465 | A1 | 6/2002 | Bashford et al. |
| 2002/0099323 | A1 | 7/2002 | Dev et al. |
| 2002/0111777 | A1 | 8/2002 | David |
| 2002/0133129 | A1 | 9/2002 | Arias et al. |
| 2002/0183647 | A1* | 12/2002 | Gozani et al. ............ 600/554 |
| 2002/0183804 | A1 | 12/2002 | Malaney et al. |
| 2003/0028072 | A1 | 2/2003 | Fischell et al. |
| 2003/0144625 | A1 | 7/2003 | Sherman et al. |
| 2003/0158583 | A1 | 8/2003 | Burnett et al. |
| 2003/0158585 | A1 | 8/2003 | Burnett |
| 2003/0216729 | A1 | 11/2003 | Marchitto et al. |
| 2003/0217754 | A1 | 11/2003 | Thomas et al. |
| 2004/0010276 | A1 | 1/2004 | Jacobs et al. |
| 2004/0054393 | A1 | 3/2004 | Stemme et al. |
| 2004/0082875 | A1 | 4/2004 | Donoghue et al. |
| 2004/0092860 | A1 | 5/2004 | Dev et al. |
| 2004/0111139 | A1 | 6/2004 | McCreery |
| 2004/0122787 | A1 | 6/2004 | Avinash et al. |
| 2004/0127939 | A1 | 7/2004 | Grey |
| 2004/0138517 | A1 | 7/2004 | Osorio et al. |
| 2004/0146611 | A1 | 7/2004 | Arias et al. |
| 2004/0147964 | A1 | 7/2004 | Nolan et al. |
| 2004/0173220 | A1 | 9/2004 | Harry et al. |
| 2004/0210254 | A1 | 10/2004 | Burnett et al. |
| 2004/0210282 | A1 | 10/2004 | Flock et al. |
| 2005/0021104 | A1 | 1/2005 | Dilorenzo |
| 2005/0029223 | A1 | 2/2005 | Yeshurun |
| 2005/0099290 | A1 | 5/2005 | Govari |
| 2005/0143783 | A1 | 6/2005 | Boveja et al. |
| 2005/0143789 | A1 | 6/2005 | Whitehurst et al. |
| 2005/0171576 | A1 | 8/2005 | Williams et al. |
| 2005/0203602 | A1 | 9/2005 | Wallace et al. |
| 2005/0277998 | A1 | 12/2005 | Tracey et al. |
| 2005/0283202 | A1 | 12/2005 | Gellman |
| 2006/0004244 | A1 | 1/2006 | Phillips et al. |
| 2006/0016452 | A1 | 1/2006 | Goetz et al. |
| 2006/0030845 | A1* | 2/2006 | Leung et al. ............ 606/41 |
| 2006/0047316 | A1 | 3/2006 | Fischell et al. |
| 2006/0049957 | A1 | 3/2006 | Surgenor et al. |
| 2006/0052839 | A1 | 3/2006 | Kim et al. |
| 2006/0084938 | A1 | 4/2006 | Zhang et al. |
| 2006/0122454 | A1 | 6/2006 | Riehl et al. |
| 2006/0122660 | A1 | 6/2006 | Boveja et al. |
| 2006/0135844 | A1 | 6/2006 | Alekseyenko |
| 2006/0161039 | A1 | 7/2006 | Juliana et al. |
| 2006/0173261 | A1 | 8/2006 | Kall et al. |
| 2006/0199159 | A1 | 9/2006 | Ghiron et al. |
| 2006/0276702 | A1 | 12/2006 | Mcginnis |
| 2007/0021712 | A1 | 1/2007 | Bernard et al. |
| 2007/0021803 | A1 | 1/2007 | Deem et al. |
| 2007/0027353 | A1 | 2/2007 | Ghiron et al. |
| 2007/0027354 | A1 | 2/2007 | Riehl et al. |
| 2007/0027355 | A1 | 2/2007 | Riehl et al. |
| 2007/0142885 | A1 | 6/2007 | Hantash et al. |
| 2007/0208212 | A1 | 9/2007 | Dilorenzo |
| 2007/0250162 | A1 | 10/2007 | Royalty |
| 2007/0265489 | A1 | 11/2007 | Fowler et al. |
| 2007/0265675 | A1* | 11/2007 | Lund et al. ............ 607/41 |
| 2007/0276318 | A1 | 11/2007 | Henley |
| 2007/0282246 | A1 | 12/2007 | Henley |
| 2008/0004484 | A1 | 1/2008 | Wieraszko et al. |
| 2008/0058874 | A1 | 3/2008 | Westlund et al. |
| 2008/0063866 | A1 | 3/2008 | Allen et al. |
| 2008/0114199 | A1 | 5/2008 | Riehl et al. |
| 2008/0177128 | A1 | 7/2008 | Riehl et al. |
| 2008/0177347 | A1 | 7/2008 | Tehrani et al. |
| 2008/0183070 | A1 | 7/2008 | Unal et al. |
| 2008/0200748 | A1 | 8/2008 | Testani et al. |
| 2008/0224808 | A1 | 9/2008 | Ghiron et al. |
| 2008/0262287 | A1 | 10/2008 | Dussau |
| 2008/0288035 | A1 | 11/2008 | Gill et al. |
| 2008/0300655 | A1 | 12/2008 | Cholette |
| 2008/0306325 | A1 | 12/2008 | Burnett et al. |
| 2008/0312725 | A1 | 12/2008 | Penner |
| 2009/0030337 | A1 | 1/2009 | Gozani et al. |
| 2009/0054950 | A1 | 2/2009 | Stephens |
| 2009/0073991 | A1 | 3/2009 | Landrum et al. |
| 2009/0076336 | A1 | 3/2009 | Mazar et al. |
| 2009/0076340 | A1 | 3/2009 | Libbus et al. |
| 2009/0076344 | A1 | 3/2009 | Libbus et al. |
| 2009/0076345 | A1 | 3/2009 | Manicka et al. |
| 2009/0076363 | A1 | 3/2009 | Bly et al. |
| 2009/0076364 | A1 | 3/2009 | Libbus et al. |
| 2009/0076397 | A1 | 3/2009 | Libbus et al. |
| 2009/0076410 | A1 | 3/2009 | Libbus et al. |
| 2009/0076559 | A1 | 3/2009 | Libbus et al. |
| 2009/0076565 | A1 | 3/2009 | Surwit |
| 2009/0118777 | A1 | 5/2009 | Iki et al. |
| 2009/0132018 | A1 | 5/2009 | DiUbaldi et al. |
| 2009/0162570 | A1 | 6/2009 | Swenberg et al. |
| 2009/0171236 | A1 | 7/2009 | Davies |
| 2009/0227829 | A1 | 9/2009 | Burnett et al. |
| 2009/0227831 | A1 | 9/2009 | Burnett et al. |
| 2009/0234179 | A1 | 9/2009 | Burnett et al. |
| 2009/0234410 | A1 | 9/2009 | Libbus et al. |
| 2009/0264792 | A1 | 10/2009 | Mazar |
| 2009/0292194 | A1 | 11/2009 | Libbus et al. |
| 2010/0022864 | A1 | 1/2010 | Cordero et al. |
| 2010/0049021 | A1 | 2/2010 | Jina et al. |
| 2010/0056881 | A1 | 3/2010 | Libbus et al. |
| 2010/0057149 | A1 | 3/2010 | Fahey |
| 2010/0160712 | A1 | 6/2010 | Burnett et al. |
| 2010/0161005 | A1 | 6/2010 | Wahlgren et al. |
| 2010/0168501 | A1 | 7/2010 | Burnett et al. |
| 2010/0204538 | A1 | 8/2010 | Burnett et al. |
| 2010/0222629 | A1 | 9/2010 | Burnett et al. |
| 2010/0222630 | A1 | 9/2010 | Mangrum et al. |
| 2010/0318009 | A1 | 12/2010 | Stanley |
| 2011/0021863 | A1 | 1/2011 | Burnett et al. |
| 2011/0264163 | A1 | 10/2011 | Tracey et al. |
| 2011/0295100 | A1 | 12/2011 | Hedge et al. |
| 2012/0059432 | A1 | 3/2012 | Emborg et al. |
| 2012/0302821 | A1 | 11/2012 | Burnett |
| 2013/0006322 | A1 | 1/2013 | Tai |

FOREIGN PATENT DOCUMENTS

| | | |
|---|---|---|
| GB | 2336544 | 10/1999 |
| JP | 2000-254239 | 9/2000 |
| WO | WO 03/070317 | 8/2003 |

(56) References Cited

FOREIGN PATENT DOCUMENTS

| WO | WO 2006/061688 | 6/2006 |
| WO | WO 2008/032279 | 3/2008 |
| WO | WO 2008/042902 | 4/2008 |
| WO | WO 2008/115426 | 9/2008 |
| WO | WO 2010/047599 | 4/2010 |
| WO | WO 2011/011748 | 1/2011 |
| WO | WO 2011/011749 | 1/2011 |
| WO | WO 2011/053607 | 5/2011 |
| WO | WO 2011/053661 | 5/2011 |
| WO | WO 2011/150332 | 12/2011 |
| WO | WO 2012/040243 | 3/2012 |

OTHER PUBLICATIONS

"Bioflex® RX754P, Single Coated Medical Pressure Sensitive Adhesive Tape," Technical Data, 2 pages, Dec. 2005.

3M Corporation, 3M™ XYZ/Isotropic Electrically Conductive Adhesive Transfer Tape 9707, 3M Electronics Markets Materials Division, 60-5002-0350-4, 8 pages, 2004, 3M.

Aaron, Roy K. et al., "Therapeutic Effects of Electromagnetic Fields in the Stimulation of Connective Tissue Repair," *Journal of Cellular Biography*, 52(1):42-6, May 1993, Wiley-Liss, Inc.

AmGel Technologies, "AG603 Sensing Gel, Sensing Gel Designed for ECG Applications," AG603-3/10, 1 page, 2010.

AmGel Technologies, "AG702 Stimulating Gel, Stimulating Gel Designed for carbon film," AG702-02/06, 1 page, 2006.

AmGel Technologies, "AG902-184/229 Grounding Gel, Grounding Gel Designed for Electrosurgical Pads," AG902 Series, 1 page, 2010.

AmGel Technologies, "Release Films," 1 Page, Jul. 25, 2006, Revision 1.

Balmaseda, Marion T. Jr., et al., "Burns in Functional Electric Stimulation: Two Case Reports," *Archives of Physical Medicine and Rehabilitation*, vol. 38., pp. 452-453, Jul. 1987.

Biowave Corporation, "510(k) Summary for the Biowave Deepwave Neuromodulation Pain Therapy Device," 6 pages, Appendix B, Dec. 13, 2005.

Biowave Corporation, "510(k) Summary for the Biowave Deepwave Neuromodulation Pain Therapy Device," 7 pages, Appendix E, Aug. 15, 2006.

Biowave Corporation, "Percutaneous Neuromodulation Pain Therapy System," *deepwave*, RevB/080926, 2008.

BlueCross BlueShield of Kansas City, "Percutaneous Electrical Nerve Stimulation (PENS) and Percutaneous Neuromodulation Therapy (PNT)," 7 pages, 1988.

Bodhale, D.W. et al., "Design, fabrication and analysis of silicon microneedles for transdermal drug delivery applications," *Proceedings of the 3rd International Conference on the Development of BME in Vietnam*, pp. 84-88, Jan. 11-14, 2010.

Bruce, C.J. et al., "Intracardiac Echocardiography," *European Journal Echocardiography*, vol. 2, pp. 234-244, 2001, The European Society of Cardiology.

Cabodevila, G. et al., "An overview on drug delivery using microneedles", Institute FEMTO-ST, Dept LPMO, 24 pages, Oct. 2005, Workshop Micro Dosing Systems.

Choi, S. et al., "Microneedle Electrode Array for Electroporation of Skin for Gene Therapy," 2 pages, 2005, Controlled Release Society 32nd Annual Meeting and Exposition Transactions.

Curley, S. et al., "Radiofrequency Ablation of Unresectable Primary and Metastatic Hepatic Malignancies," *Annals of Surgery*, vol. 230(1):1-8, 1999 Lippincott Williams & Wilkins, Inc.

CystoMedix, Inc., "Percutaneous Tibial Nerve Stimulation via Urgent® PC Neuromodulation System—An Emerging Technology for managing Overactive Bladder," *Business Briefing: Global Surgery*, 6 pages, 2004.

Fallon Community Health Plan, "Spinal Cord Stimulation," 4 pages, 2006.

Grundfest H. et al., "Stainless Steel Micro-Needle Electrodes Made by Electrolytic Pointing," *Review of Scientific Instruments*, vol. 21(4):2 pages, 1950, American Institute of Physics.

Harvinder S. Gill et al., "Effect of microneedle design on pain in human subjects," *NIH Public Access Author Manuscript*, 24(7): 585-594, Sep. 2008, Clinical Journal of Pain.

Huber, D.E. et al., "Popliteal Vein Compression Under General Anaesthesia," *European Journal of Vascular and Endovascular Surgery*, vol. 37, pp. 464-469, 2009, Elsevier Ltd.

Jacobson, Jerry I. et al., "Low-Amplitude, Extremely Low Frequency Magnetic Fields for the Treatment of Osteoarthritic Knees: A Double-Blind Clinical Study," *Electromagnetic Fields and Human Health. Fundamental and Applied Research*, pp. 363-364, Sep. 17-24, 2002, Proceedings of the Third International Conference.

Jasper, H. et al., "Unipolar Electromyograms of Normal and Denervated Human Muscle," pp. 231-244, Oct. 12, 1948, Department of Neurology and Neurosurgery, McGill University, and Montreal Neurological Institute.

Kurtzke, John F., "Epidemiology of Spinal Cord Injury," *IV Panamerican Congress of Neurology*, 18(2-3): 157-90, 93, 1975.

Lin et al., "Magnetic Stimulation of the Bladder in Dogs," AAEM Annual Meeting 1993, *Muscle & Nerve*, Oct. 1993 (Abstract).

Luttge, R. "Microneedle array electrode for human EEG recording," IFMBE Proceedings 22, pp. 1246-1249, 2008, Springer-Verlag Berlin Heidelberg 2009.

Maass et al., "Contactless Nerve Stimulation and Signal Detection by Inductive Transducer," *Symposium on Application of Magnetism in Bioengineering*, 1969.

McFarlane, J.P. et al., "Acute Suppression of Idiopathic Detrusor Instability with Magnetic Stimulation of the Sacral Nerve Roots," *British Journal of Urology*, 80(5): 734-41, Nov. 1997.

Morrison, P.R. et al., "Radiofrequency Ablation of Thoracic Lesions: Part I, Experiments in the Normal Porcine Thorax," *American Journal of Roentgenology*, 2005;184:375-380, Feb. 2005, American Roentgen Ray Society.

NeuroStar TMS Therapy, NeuroStar TMS Therapy® Recipient of Medical Design Excellence Award, *PRNewswire*, 3 pages, Apr. 2009.

Newmark, Inc., "Standard Products, Highest Quality Components, Designed & Produced Exclusively for Electrode Manufacturers," *Innovation by Design Newmark*, 2 pages, www.newmarkine.com/std_prods.htm, printed on May 3, 2010.

Noble, J.H. et al., "Automatic segmentation of the facial nerve and chorda tympani in CT images using spatially dependent features values", Medical Phsysics, vol. 35(12), pp. 5375-5384, Dec. 2008, American Association Physical Medicine.

Patel, G. et al., "Microneedles: The option for painless delivery," www.pharmainfo.net/reviews/microneedles-option-painless-delivery, 6 pages, printed on Sep. 9, 2008.

*PubMed*, U.S. National Library of Medicine National Institutes of Health, microneedle array electrode—Pub Med results, www.ncbi.nlm.nig.gov/sites/entrez, 2 pages, Search performed on Apr. 22, 2010.

*PubMed*, U.S. National Library of Medicine National Institutes of Health, microneedle electrode—Pub Med results, www.ncbi.nlm.nig.gov/sites/entrez, 7 pages, Search performed on Apr. 22, 2010.

Schaefer, O. et al., "CT-guided radiofrequency ablation of a bronchogenic carcinoma," *The British Journal of Radiology*, 76 (2003), pp. 268-270, 2003, The British Institute of Radiology.

Shafik, Ahmed, "Magnetic Stimulation: A Novel Method for Inducing Evacuation of the Neuropathic Rectum and Urinary Bladder in a Canine Model," *Urology* 54(2): 368-372, Aug. 1999.

Sheridan, MT. et al., "Pretreatment apoptosis in carcinoma of the cervix correlates with changes in tumour oxygenation during radiotherapy," *British Journal of Cancer*, 82(6):1177-1182, 2000 Cancer Research Campaign.

Sivagangabalan, G. et al., "Comparison of Electroanatomic Contact and Noncontact Mapping of Ventricular Scar in a Postinfarct Ovine Model With Intramural Needle Electrode Recording and Histological Validation," *Circulation: Arrhythmia and Electrophysiology, Journal of the American Heart Association*, vol. 1:363-369, 2008, American Heart Association.

Solbiati, L. et al., "Percutaneous US-guided Radio-Frequency Tissue Ablation of Liver Metastases: Treatment and Follow-up in 16 Patients," *Radiology*, 202(1):195-203, 1997 L.S. RSNA.

The Magstim Company Ltd, "Air Film Coil," *Magstim*, 4 pages, 2007.

(56) References Cited

OTHER PUBLICATIONS

Thon, W.F. et al., "Neuromodulation of voiding dysfunction and pelvic pain," *World Journal of Urology*, vol. 9: pp. 138-141, 1991, Springer-Verlag.

Trock, David H., "Electromagnetic Fields and Magnets Investigational Treatment for Musculoskeletal Disorders," *Rheumatic Diseases Clinics of North America*, vol. 26, No. 1., Feb. 2000.

Trock, David H., et al., "The Effect of Pulsed Electromagnetic Fields in the Treatment of Osteoarthritis of the Knee and Cervical Spine. Report of Randomized, Double Blind, Placebo Controlled Trials," *The Journal of Rheumatology*, 1903-1911, 1994.

vanSonnenberg, E. et al., "Radiofrequency Ablation of Thoracic Lesions: Part 2, Initial Clinical Experience—Technical and Multidisciplinary Considerations in 30 Patients," *American Journal of Roentgenology*, 2005;184:381-390, Feb. 2005, American Roentgen Ray Society.

Wanich, T. et al, "A Randomized Placebo-Controlled Study to Determine Safety and Efficacy in Terms of Pain Reduction, Increased Range of Motion, and Reduced Pain Medications, for a Novel Percutaneous Neuromodulation Pain Therapy Device ("Deepwave®") Following Post-Operative Treatments for Total Knee Replacement Procedures, American Academy of Orthopaedic Surgeons 2009 Annual Meeting", 6 pages, Feb. 25-28, 2008, Biowave Corporation.

Warwick, K. et al., "The Application of Implant Technology for Cybernetic Systems," *Archives of Neurology*, vol. 60:1369-1373, Oct. 2003, American Medical Association.

Wijkstrda et al., "Selective Stimulation and Blocking of Sacral Nerves: Research Setup and Preliminary Results," *Annual International Conference of the IEEE Engineering in Medicine and Biology Society*, vol. 13, No. 2, 1991.

Wilke, N. et al., "Fabrication and Characterisation of Microneedle Electrode Arrays using Wet Etch Technologies," 5 pages, Oct. 20-21, 2004, EMN04, NMRC, University College.

Zhao, M., "Genetic Analysis of Electric Signal-directed Cell Movement," 33 pages, Apr. 8, 2008, Modelling Complex Biological Systems in the Context of Genomics.

Zoll Lifecor Corporation, "What is the LifeVest Wearable Defibrillator," http://www.lifecor.com/about_lifevest/about.asp#, 1 page, printed on Jan. 7, 2011.

* cited by examiner

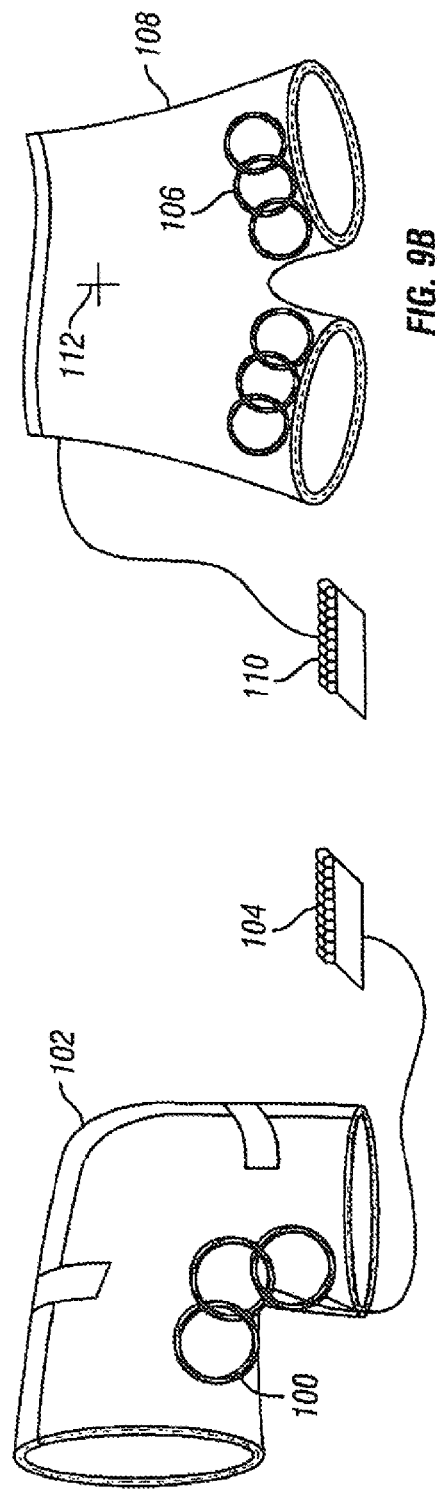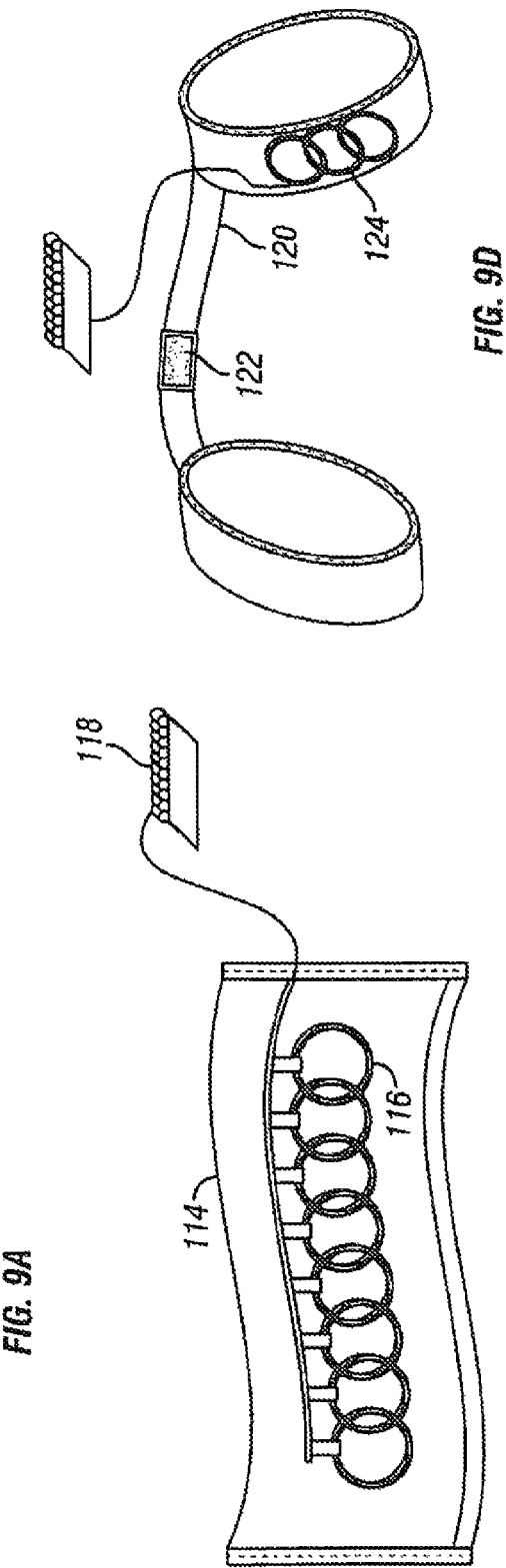
FIG. 9A  FIG. 9B  FIG. 9C  FIG. 9D

METHOD AND APPARATUS FOR ELECTRICAL STIMULATION THERAPY

CROSS-REFERENCE TO RELATED APPLICATIONS

This application is a continuation of PCT International Patent Application Number PCT/US2010/054353, filed Oct. 27, 2010, which is a continuation in part of U.S. patent application Ser. No. 12/606,941, filed Oct. 27, 2009, which is a continuation in part of U.S. patent application Ser. No. 11/866,329, filed Oct. 2, 2007, which claims the benefit of priority to U.S. Provisional Application No. 60/848,720, filed Oct. 2, 2006, the contents of which are incorporated herein by reference in their entirety.

BACKGROUND

Overactive bladder ("OAB") and urinary incontinence ("UI") affect over 16% of the American population each year, or approximately 34 million men and women. Outside of the United States, OAB and UI affects over 46 million Europeans. The economic cost of OAB and UI is estimated to be in excess of $12 billion a year in the United States alone.

Due to the social stigmas attached to OAB and UI and to misunderstandings related to the symptoms associated with OAB and UI, only 40% of the affected individuals in the United States seek medical treatment. Of those 13.6 million Americans seeking medical treatment, nearly 30% or 4 million individuals are reportedly unsatisfied with their current therapy.

Known treatments for OAB and UI include exercise and behavioral modifications, pharmacological therapies, surgical intervention and neuromodulation, but each of these treatments exhibits severe limitations.

Exercise and behavioral modifications often require patients to adhere to stringent routines, including scheduled voiding, maintenance of a bladder diary, and intense exercise regimens. While this type of treatment may be a viable option for a small group of highly dedicated individuals, its daily impact on a person's life makes it unattractive for most patients.

Pharmacological intervention is the most widely prescribed therapy for OAB and UI. Unfortunately, patients often suffer from side effects related to their drug therapies. Such side effects are sometimes serious and are particularly pronounced in elderly patient populations that tend to use a plurality of medications. In addition, approximately 30% of all patients subjected to pharmacological therapies appear to be dissatisfied with the efficacy of their prescribed treatments.

Surgical intervention IS extremely invasive and often results in a long-term requirement for catheterization that may become permanent in some instances. The negative impact of these procedures on the patient's quality of life and their high expense make surgical intervention a recommended option only when all other treatment options have been exhausted.

Neuromodulation is another available therapy for OAB and UI. In general, pulsed electromagnetic stimulation ("PES") has proven to have beneficial effects in a variety of medical applications. The related scientific principle is that an electric current passing through a coil generates an electromagnetic field, which induces a current within a conductive material placed inside the electromagnetic field.

More particularly, PES has been shown to be an effective method of stimulating a nerve positioned within the electromagnetic field, thereby affecting a muscle controlled by that nerve. For example, in the paper titled "Contactless Nerve Stimulation and Signal Detection by Inductive Transducer" presented at the 1969 Symposium on Application of Magnetism in Bioengineering, Maass et al. disclosed that a nerve threading the lumen of a toroid could be stimulated by a magnetic field of 0.7 Volt peak amplitude and a 50 µs duration in a monitor wire, and that such stimulation could generate a contraction of major leg muscles in anesthetized mammals.

Various attempts were made to use PES for treating a variety of ailments. For example, U.S. Pat. No. 4,548,208 to Niemi discloses an apparatus for inducing bone growth by generating an electric current in the body through the external application of an electromagnetic field. Such apparatus includes opposing clamps disposed on a limb and may optionally include feedback coils and a microprocessor for sensing the magnetic field, so to avoid an overcurrent mode. Therefore, this apparatus optimizes the magnetic field on the basis of measurements of the generated magnetic field.

U.S. Pat. No. 4,940,453 to Cadwell discloses a method and apparatus for magnetically stimulating the neural pathways of a higher level organism. A sinusoidally fluctuating current flow is created through a coil that overlies neurons to be stimulated, and frequency of the current flow and frequency of the magnetic field produced by the coil predetermined to correspond to the time constant of the neurons to be stimulated. Sensors for sensing coil conditions, such as coil temperature, may also be included.

U.S. Pat. No. 5,000,178 to Griffith discloses an electrical to electromagnetic transducer for applying electromagnetic energy to damaged parts of a living body by directing electromagnetic radiation to a certain damaged body part. Electromagnetic radiation is initially generated by a dipole consisting of a bar of high permeability material wrapped with an electrically conductive coil. Magnetic fields, which are generated away from the damaged body part, intersect a conductive shield and establish eddy currents, which in turn generate magnetic fields opposite and nearly equal to the magnetic fields generated by the electromagnetic source. The resultant electromagnetic fields reinforce the electromagnetic field directed towards the damaged body part and diminish the electromagnetic field directed away from the damaged body part.

U.S. Pat. No. 5,014,699 to Pollack et al. discloses a non-invasive, portable electromagnetic therapeutic method and apparatus for promoting the healing of damaged or diseased living tissue, including fractured bone. These method and apparatus involve generating a signal that has a series of substantially symmetric voltage cycles of bursted pulses with narrow pulse widths of 0.5 to 20 microseconds, and further involve converting the signal into an electromagnetic field extending into an area that contains tissue to be healed. It provides for no feedback on the efficiency of the applied stimulation.

In a paper titled "Selective Stimulation and Blocking of Sacral Nerves: Research Setup and Preliminary Results," published in Annual International Conference of the IEEE Engineering in Medicine and Biology Society, Vol. 13, No. 2, 1991, Wijkstrda et al. used an external pulsed magnetic coil to stimulate a peripheral nerve for the treatment of urinary incontinence. The authors used a large magnetic field produced by a single coil to ensure that the nerve was fired and the resulting nerve conduction was frequently painful or intolerable. In addition, coil alignment was problematic because an internally implanted coil was utilized, which had to be aligned with the fully external magnetic field to stimulate the nerve. Due to the difficulty in positioning the device, the practical application of this therapy does not permit home healthcare usage without a preset alignment and monitoring of the nerve, and no provision was made to insure that the nerve was actually being stimulated or to adjust the device in response to commonly occurring physiologic and anatomic variations in nerve locations.

U.S. Pat. No. 5,181,902 Erickson et al. and U.S. Pat. No. 5,314,401 to Tepper disclose pulsed electromagnetic field ("PEMF") transducer systems usable to perform PEMF therapies (such as after spinal fusion) by generating flux-aided electromagnetic fields. The drive electronics includes a PEMF processor that executes a PEMF program for controlling the activation of the electromagnetic fields (field strength and cycle).

In a paper titled: "Magnetic Stimulation of the Bladder in Dogs" presented at the 1993 AAEM Annual Meeting, the abstract of which was published in the Muscle & Nerve issue of October 1993, Lin et al. disclosed that magnetic stimulation could be employed to stimulate the cortex, spinal nerves and peripheral nerves of dogs through direct trans-abdominal stimulation of the detrusor muscles or through stimulation of the lumbosacral roots.

As shown, however, there has been no provision made to measure the efficacy of PES treatment, causing patients to be treated improperly, either by an insufficient or excessive exposure to PES. Other attempts to monitor PES dosage exhibit serious drawbacks. For example, U.S. Pat. No. 5,518,495 to Kot discloses an apparatus for the treatment of arthritis utilizing a magnetic field therapy, which includes an adjustable voltage source that is connected to a source of line voltage and a coil connected to the adjustable voltage source. This apparatus has no feedback system to advise a healthcare provider of the efficiency of the treatment.

U.S. Pat. No. 5,984,854 to Ishikawa et al. discloses a method for treating urinary incontinence based on delivering a train of current pulses through one or more magnetic stimulation coils so to induce a train of magnetic flux pulses, which then induce an eddy current within the body and stimulates a group of pelvic floor muscles, the pudendal nerve, the external urethral sphincter, or the tibial nerve. While this method includes the use of pulsed electromagnetic for treating urinary incontinence, no specific components are envisioned to facilitate the placement of the magnetic coils over a targeted region of the body or a system for monitoring the efficiency of the therapy being applied.

U.S. Pat. No. 6,086,525 to Davey et al. discloses a magnetic nerve stimulator that includes a core constructed from a material having a high field saturation having a coil winding disposed thereon. A thyristor capacitive discharge circuit pulses the device, and a rapidly changing magnetic field is guided by the core, preferably made from vanadium permendur.

U.S. Pat. No. 6,701,185 to Burnett et al. also discloses an electromagnetic stimulation device that includes a plurality of overlapping coils, which can be independently energized in a predetermined sequence such that each coil will generate its own independent electromagnetic field and significantly increase the adjacent field. Unfortunately, none of these patents provides a system for monitoring the efficiency of the therapy in progress, either with respect to the proper positioning of the winding over the area to be treated or of the intensity of the magnetic field to be applied.

Other PES therapies require the implantation of devices into the patient, with the consequent discomfort, risk and cost to the patient. For example, U.S. Pat. No. 6,735,474 to Loeb et al. discloses a method and system for treating UI and/or pelvic pain by injecting or laparoscopically implanting one or more battery- or radio frequency-powered microstimulators that include electrodes placed beneath the skin of the perineum and/or adjacent the tibial nerve.

U.S. Pat. No. 6,941,171 to Mann et al. describes a method and a system for treating incontinence, urgency, frequency, and/or pelvic pain that includes implantation of electrodes on a lead or a discharge portion of a catheter adjacent the perineal nerve(s) or tissue(s) to be stimulated. Stimulation pulses, either electrical or drug infusion pulses, are supplied by a stimulator implanted remotely through the lead or catheter, which is tunneled subcutaneously between the stimulator and stimulation site.

Other PES therapies involve the use of electrodes placed on or beneath the skin of a patient. Recent data on invasive, needle-based PES of the posterior tibial nerve in individuals with OAB and UI indicates that PES can modulate bladder dysfunction through its action on the pudendal nerve and the sacral plexus, which provide the major excitatory input to the bladder.

In a paper titled "Percutaneous Tibial Nerve Stimulation via Urgent® PC Neuromodulation System—An Emerging Technology for managing Overactive Bladder," which was published in Business Briefing: Global Surgery 2004, CystoMedix, Inc. disclosed that peripheral tibial nerve stimulation ("PTNS") had been found effective in treating OAB. The disclosed procedure involved the use of electrode and generator components, including a small 34-gauge needle electrode, lead wires and a hand-held electrical generator. However, the procedure requires the permanent implantation of an electrical stimulation device in the patient. One estimate put the cost of treatment at nearly $14,000 with additional routine care costs of $593 per patient per year. Additionally, risks of battery failure implant infection, and electrode migration led to a high re-operation rate and made this procedure unattractive.

U.S. Pat. No. 7,117,034 to Kronberg discloses a method for generating an electrical signal for use in biomedical applications that includes two timing-interval generators. Skin-contact electrodes may be placed over an area of interest and a microprocessor may direct timing and sequencing functions, although such timing and sequencing functions are not related to the actual efficacy of the treatment while treatment is being performed.

U.S. Patent Application Publication No. 2005/0171576 to Williams et al. discloses an electro-nerve stimulation apparatus that includes a pulse generator, a first electrically conductive, insulated lead wire, a second electrically conductive, insulated lead wire, an electrically conductive transcutaneous electrode and an electrically conductive percutaneous needle electrode. Connected to one end of the first and second lead wires is a connector for electrically coupling with the pulse generator. A percutaneous needle electrode is inserted through the skin in proximity to the desired internal stimulation site and electric stimulation is employed, rather than pulsed electromagnetic stimulation. Moreover, Williams does not contemplate mechanisms for facilitating use of the device by an untrained user, nor a monitoring of the applied therapy.

A neuromodulation alternative is a posterior tibial nerve stimulator, often referred to as SANS, but as is the case with other forms of neuromodulation, this procedure is invasive in nature and requires the insertion of a needle five centimeters into the patient's ankle region to stimulate the posterior tibial nerve. This procedure also requires a minimum of twelve sessions for initial treatment, possibly with additional sessions required for maintenance.

SUMMARY

Energy emitting systems and methods for providing a medical therapy are provided. In certain embodiments, the energy emitting system may include a conductive coil configured to generate a magnetic or electromagnetic field focused on a target nerve. The conductive coil may be adjustable and include a first end, a second end, and one or more turns positioned there between where the first turn surrounds a central aperture. The central aperture may be adjustable or movable between a first configuration and a second configuration where the second configuration has a radius that is greater than the radius of the first configuration. The adjustable or movable nature of the coil allows the conductive coil or energy emitting system to conform to, accommodate, surround or be positioned or fit on a particular anatomical structure of a patient and to thereby be positioned in proximity to the underlying target nerve.

Optionally, the conductive coil can include a hinge or other pivoting mechanism positioned along a central axis of the conductive coil. The hinge could divide the coil into a first portion and a second portion where either the first portion, second portion or both are pivotable about the hinge such that dimensions of the central aperture and the coil could be adjusted, altered, or manipulated.

In certain embodiments, a method of magnetic induction therapy includes positioning a conductive coil relative to a first portion of a patient's body in proximity to an underlying target nerve to concentrate an electromagnetic flux on the underlying target nerve. The positioning of the coil may include adjusting or manipulating the central aperture of the conductive coil, such that the conductive coil accommodates, conforms to, surrounds or is positioned or fit on or around the first portion of the patient's body. Once the coil is in place, a current is passed through the conductive coil to generate a magnetic field focused on the target nerve.

In other embodiments, an energy emitting system for providing a medical therapy can include a conductive coil configured to generate a magnetic or electromagnetic field focused on a target nerve. The conductive coil may have a first end, a second end, and one or more turns there between. The first turn surrounds a central aperture which is sized to receive a first portion of a patient's body such that the conductive coil can be positioned in proximity to the underlying target nerve.

Other features and advantages will appear hereinafter. The features and elements described herein can be used separately or together, or in various combinations of one or more of them.

BRIEF DESCRIPTION OF THE DRAWINGS

The drawings constitute a part of this specification and include exemplary embodiments of the invention, which may be embodied in various forms. It is to be understood that in some instances various aspects of the embodiments may be shown exaggerated or enlarged to facilitate an understanding of the embodiments.

FIGS. 9A-9D are schematic representations of different garments adapted to operate as apparatus for magnetic induction therapy.

FIG. 13c shows an end view of the conductive coil of FIG. 13a.

DETAILED DESCRIPTION

Detailed descriptions of various embodiments are provided herein. It is to be understood, however, that the embodiments may be embodied in various forms. Therefore, the specific details disclosed herein are not to be interpreted as limiting, but rather as a representative basis for teaching one skilled in the art how to employ the various embodiments in virtually any detailed system, structure, or manner.

Various embodiments will now be described. The following description provides specific details for a thorough understanding and enabling description of these embodiments. One skilled in the art will understand, however, that the embodiments may be practiced without many of these details. Additionally, some well-known structures or functions may not be shown or described in detail so as to avoid unnecessarily obscuring the relevant description of the various embodiments.

The terminology used in the description presented below is intended to be interpreted in its broadest reasonable manner, even though it is being used in conjunction with a detailed description of certain specific embodiments. Certain terms may even be emphasized below. Any terminology intended to be interpreted in any restricted manner, however, will be overtly and specifically defined as such in this detailed description section.

Where the context permits, singular or plural terms may also include the plural or singular term, respectively. Moreover, unless the word "or" is expressly limited to mean only a single item exclusive from the other items in a list of two or more items, then the use of "or" in such a list is to be interpreted as including (a) any single item in the list, (b) all of the items in the list, or (c) any combination of items in the list.

Figure 1:
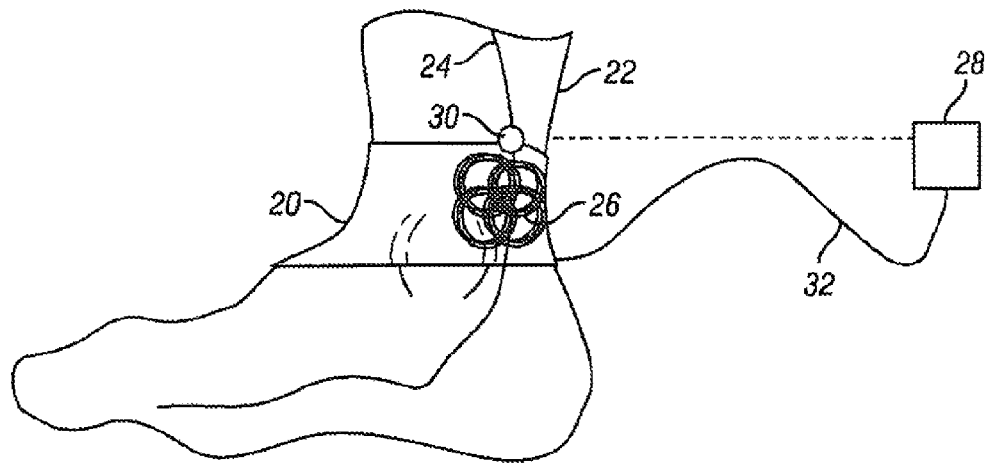
FIG. 1 is a schematic view of a variation of an apparatus for magnetic induction therapy.

Referring first to FIG. 1, a first embodiment includes a coil wrap 20, which is depicted as disposed over ankle 22 circumferentially to surround a portion of tibial nerve 24. Because tibial nerve 24 is targeted, this embodiment is particularly suited for the treatment of OAB and VI. In other embodiments, coil wrap 20 may be configured to surround other body parts that contain a portion of tibial nerve 24 or of other nerves branching from or connected to tibial nerve 24, still making these embodiments suitable for treating OAB and VI. In still other embodiments, coil wrap 20 may be configured for surrounding body parts that contain other nerves when treatments of other ailments are intended.

Coil wrap 20 may be manufactured from a variety of materials suitable for wearing over ankle 22. Preferably, coil wrap is produced from a soft, body-compatible material, natural or synthetic, for example, cotton, wool, polyester, rayon, Gore-Tex®, or other fibers or materials known to a person skilled in the art as non-irritating and preferably breathable when tailored into a garment. Coil wrap 22 may even be manufactured from a molded or cast synthetic material, such as a urethane gel, to add extra comfort to the patient by providing a soft and drapable feel. Additionally, coil wrap 20 may be produced from a single layer of material or from multiple material layers and may include padding or other filling between the layers.

Coil wrap 20 contains one or more conductive coils 26 arranged to produce a pulsed magnetic field that will flow across tibial nerve 24 and generate a current that will flow along tibial nerve 24 and spread along the length of tibial nerve 24 all the way to its sacral or pudendal nerve root origins. Coils 26 may be a single coil shaped in a simple helical pattern or as a figure eight coil, a four leaf clover coil, a Helmholtz coil, a modified Helmholtz coil, or may be shaped as a combination of the aforementioned coils patterns. Additionally, other coil designs beyond those mentioned hereinabove might be utilized as long as a magnetic field is developed that will encompass tibial nerve 24 or any other target nerve. When a plurality of coils is utilized, such coils may be disposed on a single side of ankle 22, or may be disposed on more than one side, for example, on opposing sides, strengthening and directionalizing the flow of the magnetic field through tibial nerve 24 or other peripheral nerves of interest.

Coil wrap 20 is preferably configured as an ergonomic wrap, for example, as an essentially cylindrical band that can be pulled over ankle 22, or as an open band that can be wrapped around ankle 22 and have its ends connected with a buckle, a hoop and loop system, or any other closing system known to a person skilled in the art. By properly adjusting the position of coil wrap 20 over ankle 22, a patient or a health care provider may optimize the flow of the magnetic field through tibial nerve 24, based on system feedback or on sensory perceptions of the patient, as described in greater detail below.

The electric current that produces the magnetic field by flowing through coils 26 is supplied by a programmable logic controller 28, which is connected to coils 26, for example, with a power cord 32. A sensor 30 that feeds information to logic controller 28 is also provided, in order to tailor the strength of the magnetic field and control activation of coils 26 based on nerve conduction. The purpose of sensor 30 is to detect and record the firing of the target nerve and to provide related information to logic controller 28, so to render the intended therapy most effective. For example, sensor input may cause logic controller 28 to alter the strength or pulse amplitude of the magnetic field based on sensor input, or fire the coils in a certain sequence.

In this embodiment, as well as in the other embodiments described hereinafter, sensor 30 may include one or more sensor patches and may be placed at different distances from the region of direct exposure to the magnetic field. For example, sensor 30 may be configured as a voltage or current detector in the form of an EKG patch and may be placed anywhere in the vicinity of the target nerve to detect its activation. For ease of description, the term "coils" will be used hereinafter to indicate "one or more coils" and "sensor" to indicate "one or more sensors," unless specified otherwise.

By virtue of the above described arrangement, coil wrap 20 provides a reproducibly correct level of stimulation during an initial therapy session and during successive therapy sessions, because the presence or absence of nerve conduction is detected and, in some embodiments, measured when coil wrap 20 is first fitted and fine-tuned on the patient. In addition to properly modulating the applied magnetic field, the positioning of coils 26 over ankle 22 may also be tailored according to the input provided by sensor 30, so to fine-tune the direction of the magnetic field. Such an adjustment of the direction, amplitude, and level of the stimulation provided to the target nerve through the above described automated feedback loop, to ensure that peripheral nerve conduction is being achieved can be an important feature when implemented.

If the magnetic pulse does not substantially interfere with sensor 30, sensor 30 may be placed directly within the field of stimulation, so that power supplied to the system may be conserved. This is particularly important for battery-powered systems. Alternatively, sensor 30 may also be placed at a distance from the magnetic field and still properly detect neural stimulation.

In a method of use of coil wrap 20, the amplitude and/or firing sequence of coils 26 may be ramped up progressively, so that the magnetic field is increased in strength and/or breadth until nerve conduction is detected, after which the applied stimulus is adjusted or maintained at its current level for the remainder of the therapy. The level of stimulation may be also controlled through a combination of feedback from sensor 30 and feedback based on perceptions of the patient. For example, the patient may activate a switch once she perceives an excessive stimulation, in particular, an excessive level of muscular stimulation. In one instance, the patient may be asked to push a button or turn a knob when she feels her toe twitching or when she experiences paresthesia over the sole of her foot. The patient will then continue pressing the button or keep the knob in the rotated position until she can no longer feel her toe twitching or paresthesia in her foot, indicating that that level of applied stimulation corresponds to an optimal therapy level. From that point on, the patient may be instructed to simply retain her foot, knee, or other limb within coil wrap 20 until therapy has been terminated while the system is kept at the optimal level. Adding patient input enables control of coil wrap 20 during outpatient treatments, because the patient is now able to adjust the intensity of the magnetic field herself beyond the signals provided to logic controller 28 by sensor 30.

Detecting and, if the case, measuring conduction in one or more nerves along the conduction pathways of the stimulated nerve confirms that the target nerve has been stimulated, providing an accurate assessment of the efficiency of the applied therapy on the patient. A concomitant detection of muscle contraction may also confirm that the target nerve is being stimulated and provide an indication to the patient or to a healthcare provider as to whether stimulation has been applied at an excessive level in view of the anatomical and physiological characteristics of the patient.

Based on the foregoing, coil wrap 20 allows for a consistent, user-friendly targeting and modulation of the peripheral nerves via the posterior tibial nerve on an outpatient basis, in particular, the targeting and modulation of the pudendal nerve and of the sacral plexus. When multiple coils 26 are present, coils 26 may be activated simultaneously or differentially to generate the desired magnetic field. The direction and location of each of coils 26 may be reversibly or irreversibly adjusted by the healthcare provider or by the patient, customizing the location of the applied stimulation to the anatomy and therapy needs of each patient. After a healthcare provider has optimized position and firing sequence for each of coils 26, the patient may be sent home with coil wrap 20 adjusted to consistently target the desired nerve. In one variant of the present embodiment, an automatic feedback system adjusts one or more of firing sequence, firing strength or position of coils 26 within coil wrap 20 during the initial setup and also during successive therapy sessions.

In summary, certain embodiments include the creation of a loop consisting of feeding information on nerve conduction to logic controller 28 and on logic controller 28 tailoring the electrical current sent to coil wrap 20 according to the information received from sensor 26 based on whether or not the nerve is receiving the desired stimulation and, in some embodiments, the desired amount of stimulation. This arrangement offers an unparalleled level of therapy control and flexibility within a home care setting, because a consistent, repeatable stimulation of the target nerve can be attained. Aside from adjusting the position of coils 26 in accordance with the patient's anatomy and physiological variations, controlling pulse amplitude is also of great importance even during different therapy sessions with the same patient. For example, a patient with leg edema will encounter difficulties in properly adjusting coil wrap 20 based on whether her legs and ankles are swollen or not swollen, and the power required to penetrate to posterior tibial nerve 24 (in the case of a VI therapy) will vary greatly due to the variable depth of the nerve. Thus, having feedback provided by sensor 26 becomes a necessity for achieving an accurate dosage of the treatment rather than an option. Benchtop testing has demonstrated that a system constructed according embodiments described herein is capable of non-invasively generating electrical currents similar to those found in therapeutic electro-stimulation and to do so in different settings.

Figure 2:
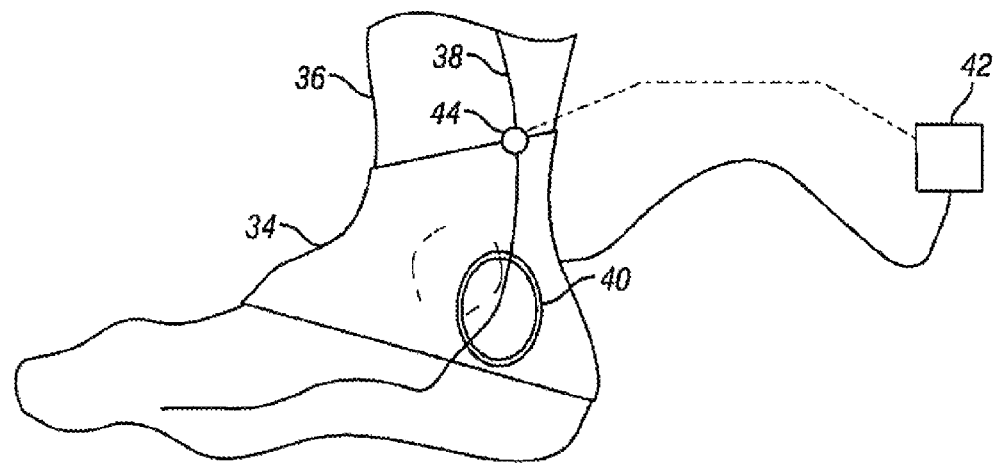
FIG. 2 is a schematic view of a variation of an apparatus for magnetic induction therapy.

Referring now to FIG. 2, a second embodiment will be described with reference to a coil wrap 34 disposed over ankle 36 for the purpose of treating VI by targeting tibial nerve 38. In this second embodiment, one or more Helmholtz coils 40 are disposed within coil wrap 34 to create a more narrowly directed magnetic field over tibial nerve 38. Like in the all other embodiments described herein, more than one coil (in the present embodiment, more than one Helmholtz coil 40) may be placed within coil wrap 34 and be disposed in different positions within coil wrap 34, in order to optimize magnetic flux over tibial nerve. For example, two Helmholtz coils may be disposed one opposite to the other within coil wrap 34.

Having coil windings arranged along a common longitudinal axis, as required in a Helmholtz coil configuration, generates a more focused magnetic field and a more accurate targeting of tibial nerve 38 or of any other nerve. Like in the previous embodiment, the operation of coils 40 is controlled by a logic controller 42, which is in turn connected to sensor 44 that monitors conduction in tibial nerve 44 and that generates a feedback to logic controller 42 about the efficiency of the therapy in progress. Therefore, like in the previous embodiment, the coupling of sensor 44 with logic controller 42 optimizes operation of coil wrap 34 according to results measured at the level of tibial nerve 38. Also like in the previous embodiment, manual adjustments to the parameters of electric current provided by logic controller 42 to Helmholtz coil 40 may also be made manually by the patient or by a healthcare provider, and coil wrap 34 may be structured so that the position of Helmholtz coil 40 within coil wrap 34 is adjusted as desired either manually by the patient or by a healthcare provider, or automatically by logic controller 42.

Figure 3:
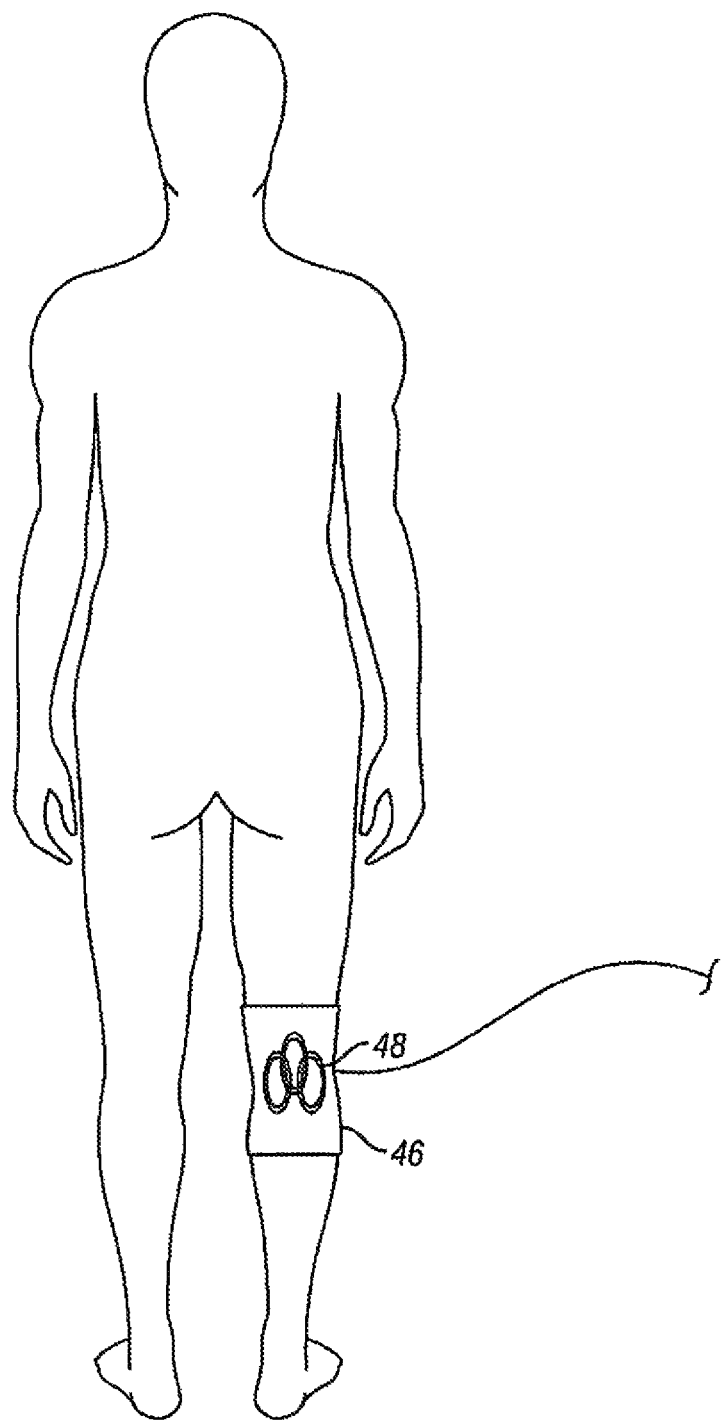
FIG. 3 is a schematic view of a variation of an apparatus for magnetic induction therapy.

Referring now to FIG. 3, a third embodiment includes a coil wrap 46 configured for wrapping over the popliteal fossa of a patient, in the region of the knee, to stimulate the posterior tibial nerve (not shown). The configuration and structure of coil wrap 46 reflect the body portion covered by coil wrap 46, but the key system components of coil wrap 46, such as the type, number and disposition of the coils (for example, the use of overlapping coils); the connections of the coils with a logic controller; and the use of one or more sensors (also not shown) to detect nerve conduction are all comparable to those in the previously described embodiments.

Figure 4:
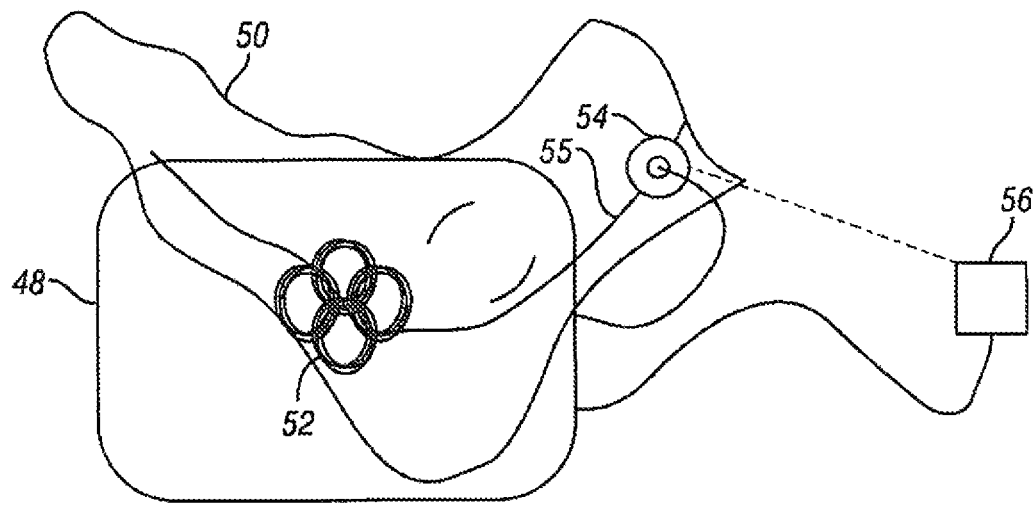
FIG. 4 is a schematic view of a variation of an apparatus for magnetic induction therapy.

Referring now to FIG. 4, a fourth embodiment includes a footrest or foot cradle 48, which is structured to contain at least a portion of a foot 50. One or more coils 52 are enclosed within cradle 48, and a sensor 54 is disposed along the pathway of tibial nerve 55, sensing conduction in tibial nerve 55, and is also connected to a logic controller 56. Coils 52, sensor 54 and logic controller 56 may be arranged in different configurations, in the same manner as in the preceding embodiments.

Cradle 48 may be made from a variety of materials and may be monolithic, or have a hollow or semi-hollow structure to enable the movement of coils 52 within cradle 48, as described in greater detail below. Preferably, cradle 48 has an ergonomically design allowing the ankle and heel of the patient to be retained within cradle 48, in a position that matches the positions of stimulating coils 52 to the area of stimulation. The design of cradle 48 provides for a particularly comfortable delivery of therapy to patients that prefer to remain seated during their therapy, and enables the patient to perform the required therapy within a health care facility, or to take cradle 48 home, typically after an initial session and appropriate training in a health care facility. In that event, the patient will be trained to apply sensor 54 autonomously and to adjust stimulation to a comfortable level.

FIG. 4 shows coils 52 disposed as overlapping and the use of a single sensor patch 54 positioned proximally to the stimulation site. However, coil 52 may be configured as a single coil, a figure eight coil, a four leaf clover coil, a Helmholtz coil, a modified Helmholtz coil or a any combination of the aforementioned coils, or as any other coil design providing an effective stimulation to the target nerve. In addition, coils 52 may be fired individually, sequentially or simultaneously according to the feedback provided by sensor 54.

In one variant of this embodiment, sensor 54 may include a conductive electrode patch that provides a feedback to logic controller 56 for adjusting, if necessary, the stimulation parameters of coils 52. Alternatively, sensor 54 may be a sensor patch that is either applied to the skin of the patient or is incorporated within the structure of cradle 48.

Figure 5:
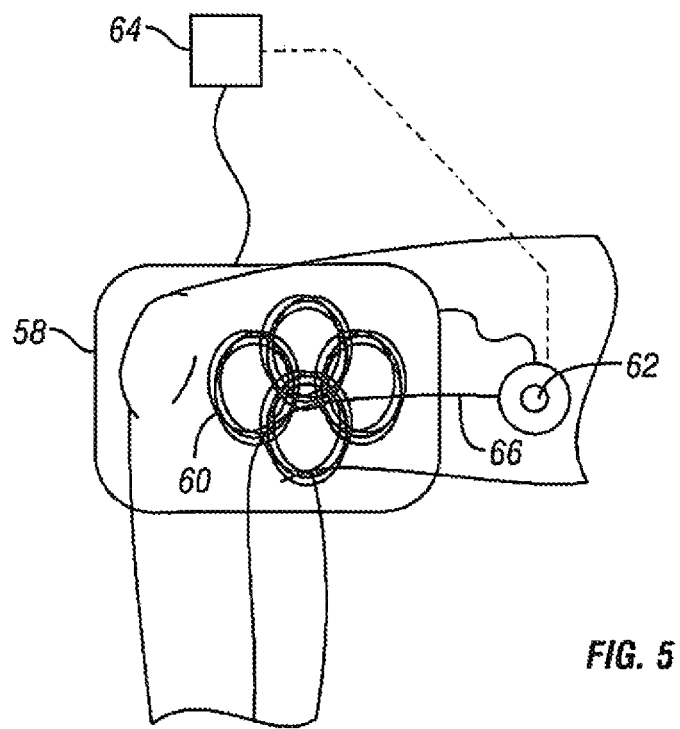
FIG. 5 is a schematic view of a variation of an apparatus for magnetic induction therapy.

Referring now to FIG. 5, a fifth embodiment includes a knee rest or knee cradle 58 that contains one or more conductive coils 60, one or more sensors 62 and a logic controller 64. The components of this embodiment are similar to those described with reference to the preceding embodiments, as regards the structure and materials of cradle 58, the nature and disposition of coils 60, the type and operation of sensor 62, and the function and operation of logic controller 64. Cradle 58 is configured to target the popliteal fossa of the patient, thus to target tibial nerve 66. In that respect, the present embodiment is similar to the embodiment illustrated in FIG. 3, but while the embodiment of FIG. 3 is configured as a wrap that may be worn while the patient is standing, the present embodiment is configured as a cradle that is more suited for treatment while the patient is sitting or laying down.

A method of use of the foot cradle depicted in FIG. 4 is described with reference to FIGS. 6A-6D. During a first step illustrated in FIG. 6A, foot 68 is disposed in cradle 70 that contains one or more conductive coils 72, which are connected to a logic controller (not shown) that manages the flow of electric power to coils 72.

Figure 6A:
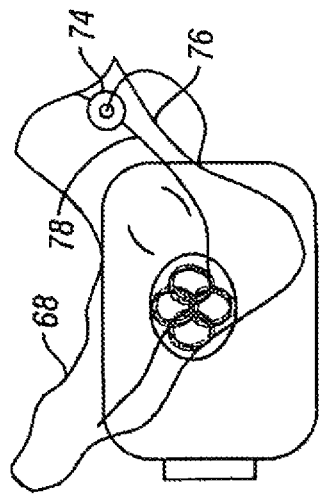
FIGS. 6A-6D are schematic illustrations depicting a first method of use of an apparatus for magnetic induction therapy. This method is based on adjusting the position of the conductive coils so to optimize a magnetic flow applied to a target nerve.
Figure 6B:
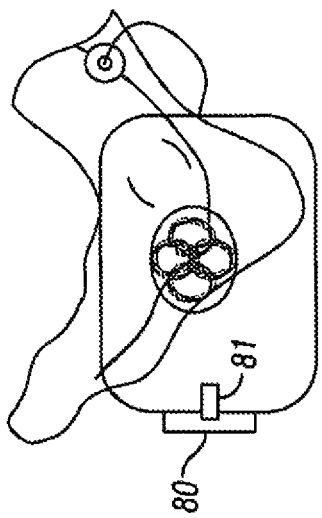

During a second step illustrated in FIG. 6B, a sensor 74 is disposed on foot 68 or on ankle 76 or on another appropriate portion of the patient's body, in order to detect conductivity in tibial nerve 78 or in another target nerve.

Figure 6C:
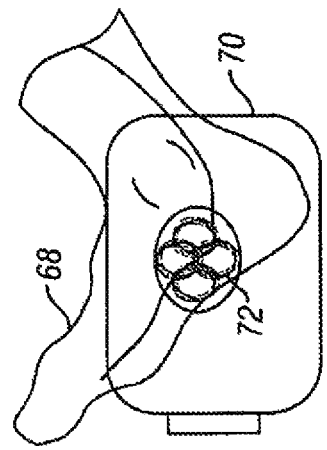

During a third step illustrated in FIG. 6C, a healthcare provider analyzes conductivity measurements provided by sensor 74 (for example, by reading gauge 77) and first adjusts the positioning of coils 72 until conduction in nerve 78 is detected. For example, the healthcare provider may rotate a knob 80, slide a lever or actuate any other displacement system for coils 72 that is known in the art, so that coils 72 are translated until a magnetic field of the proper amplitude and intensity is applied to cause conduction in nerve 78. The position of coils 72 is then fine-tuned manually until an optimal level of conduction in nerve 78 is attained, and the therapy is continued for a length of time as prescribed by the attending healthcare provider.

Figure 6D:
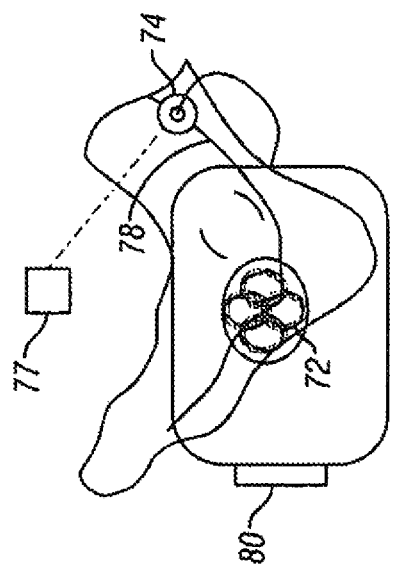

During a fourth, optional step illustrated in FIG. 6D, settings for successive therapy sessions are set, for example by locking knob 80 (in one embodiment, with a pin 81) so that the healthcare provider or the patient repeat the therapy using the predetermined settings. Alternatively, the patient may be trained to adjust the amplitude and/or strength of the applied magnetic field, as each therapy session requires.

While the present method has been described with regard to foot cradle 70, the same method steps may be envisioned for coil wraps or cradles of different configurations, for example, for the coil wraps and cradles described with reference to the previous figures.

In an alternative embodiment, the logic controller (not shown) may automatically adjust coil positioning to optimize therapy during the initial and successive sessions. While this set-up may be more difficult to implement, it also provides for an accurate targeting of the target nerve during each therapy session, regardless of alterations in patient positioning or changes to the anatomy of the patient (for example, when a foot is swollen). In this embodiment, the device simply varies the orientation of coils 84 until stimulation has been sensed.

Further, coils 84 may be translated along a single direction (for example, horizontally) or along a plurality of directions, to provide for the most accurate positioning of coils 84 with respect to the target nerve.

A second method of use of the foot cradle depicted in FIG. 4 is described now with reference to FIG. 7. While this second method is also described with reference to a foot cradle 82 employing one or more coils 84 that have a reversibly lockable, adjustable orientation, the present method may be equally implemented with a body-worn coil wrap, such as those described with reference to the previous figures, or to other embodiments. In this method, the patient or the healthcare provider adjusts the positioning of coils 84 to detect conductivity in target nerve 89.

The position of coils 84 may be translated in different directions (in the illustrated embodiment, may be translated horizontally) and may be locked in an initial position once conduction in nerve 89 is detected by a sensor (for example, sensing patch 86)

Figure 7A:
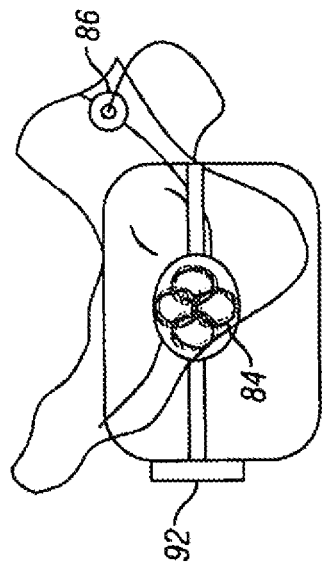
FIGS. 7A-7D are schematic illustrations of a second method of use of an apparatus for magnetic induction therapy. This method is based on locking the conductive coils in position once electrical conduction in a target nerve has been detected.
Figure 7B:
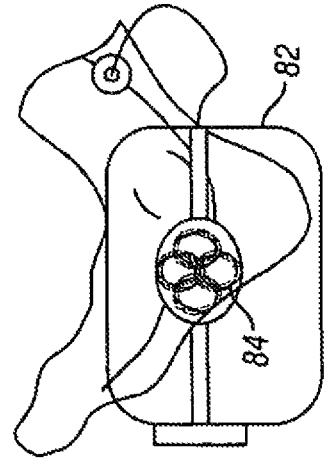

More particularly, FIG. 7A illustrates the initial positioning of foot 88 into cradle 82 and of sensor patch 86 on ankle 90 or other appropriate body part of the patient. After proper positioning of foot 88 is attained, a knob 92 (or other equivalent device) may be employed to adjust the position of coils 84, based on the signals (for example, nerve conduction signals) provided by sensor patch 86, as shown in FIG. 7B.

Figure 7C:
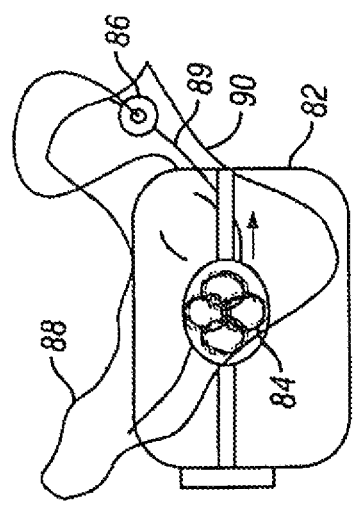
Figure 7D:
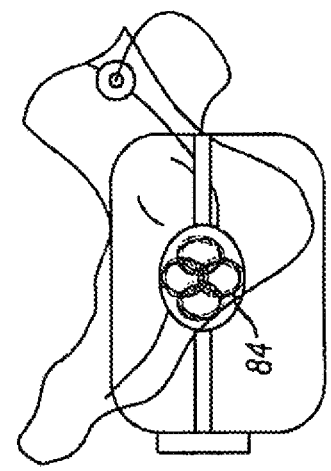

With reference to FIG. 7C, after neural conduction is detected, coils 84 are locked in place, and, with further reference to FIG. 7D, foot cradle 82 retains coils 84 locked in position for further use in a home or healthcare office environment. Therefore, in the present method, the patient or a healthcare provider simply adjusts coil position by sliding coils 84 back and along one axis until electric conduction in the target nerve is detected, although adjustments along all three axes may be possible in different variants of the present embodiment.

Figure 8:
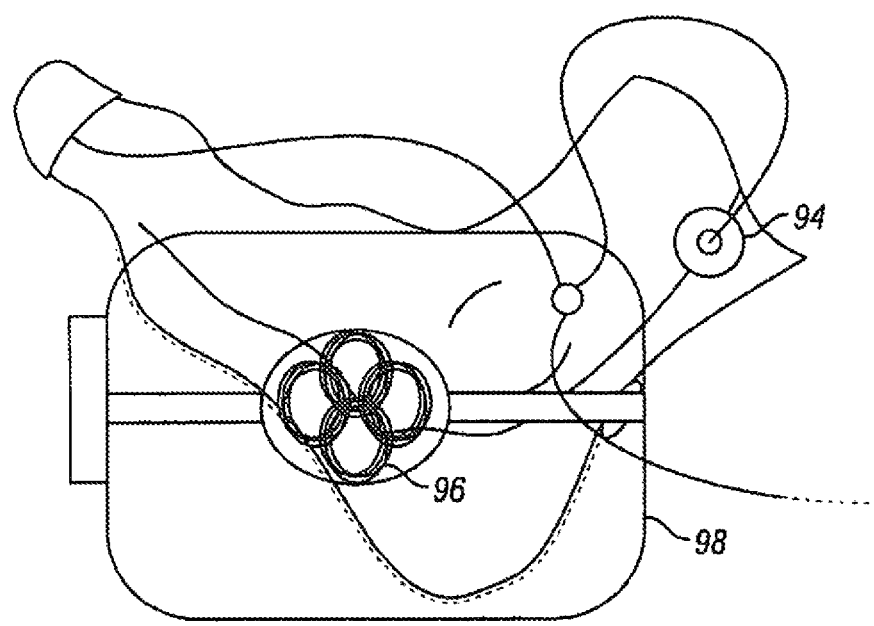
FIG. 8 is a schematic view of an embodiment that includes a plurality of sensors.

Referring now to FIG. 8, a sixth embodiment relates to the use of multiple sensors. While FIG. 8 depicts an embodiment shaped as a foot cradle 98, it should be understood that the following description also relates to any other design, whether shaped as a cradle or a wrap or otherwise. The plurality of sensors 94 described herein may detect a variety of physiologic changes, including neural impulses, muscular contraction, twitching, etc. that may occur with neural or muscular stimulation.

One or more of the illustrated sensors 94 may be employed over body regions being stimulated (for example, back, leg, arm, neck, head, torso, etc.) and may be either incorporated within an actual cradle or wrap or, otherwise, be applied separately from the cradle or the wrap.

Sensors 94 may be structured as disposable, single-use, EKG-type patches that are attached to the body outside of cradle 98 along the nerve conduction pathway and are then connected to the logic controller (not shown) before beginning therapy. This arrangement provides for an intimate body contact of sensors 94 without the risk of infection or other detrimental side effects that may be present with transcutaneous devices. Sensors 94 may be employed both for beginning and for monitoring the stimulation therapy; more specifically, sensors 94 may be employed during the beginning of the therapy to optimize the strength of the magnetic field and/or to adjust the positioning of coils 96 within the cradle 98. Once therapy has begun, sensors 94 continue to monitor nerve conduction to ensure that the correct level of stimulation is being provided. In the event that for some reason nerve conduction decays during therapy, the logic controller can automatically adjust the magnetic field, ensuring that the appropriate therapy is delivered for the appropriate amount of time.

One or more of sensors 94 in this embodiment, or any of the embodiments described herein, may take the form of an inductive coil designed to receive impulses from the underlying nerves, so that inductive technologies may be used to both stimulate the nerve or tissues as well as to record the effect of the stimulation on nerves or tissues. Any of sensors 94 may be connected to the logic controller through one or more connection modes, including, but not limited to, wireless signals, wired signals, radio frequencies, Bluetooth, infrared, ultrasound, direct switching of the current circuit, etc., so long as communication between the sensor and the device is effective.

During implementation of the present method, a healthcare provider may simply elect to use sensors 94 to adjust the device, for example, to lock coils 96 into position, during the first therapy session and not require the use of sensors 94 during each successive therapy session.

Referring now to FIGS. 9A-9D, there are shown different, non-limiting embodiments shaped as body worn ergonomic applicator garments. Each of these embodiments is shown with overlapping coils, although coils of any configurations may be used. Each of the wraps of FIGS. 9A-9D corresponds to a coil wrap, into which a body part may be placed. These garments contain one or more sensors (not shown) that provide feedback to a logic controller (also not shown), or sensors may be applied separately from those garments. Systems may also be included for reversibly or irreversibly locking the coils within the applicator.

More particularly, FIG. 9A illustrates an embodiment, in which coils 100 are embedded in a knee wrap 102 and are connected to a logic controller (not shown) by a connector 104. FIG. 9B instead illustrates an embodiment, in which coils 106 are disposed within an abdominal garment, for example shorts 108 and in which coils 106 are also connected to a logic controller (not shown) by a connector 110. A marking 112 may be added on one side of shorts 108 to indicate wrap orientation. FIG. 9C illustrates a coil wrap shaped like a band 114, in which coils 116 are connected to a logic controller (not shown) by a connector 118. When this embodiment is employed, band 114 may be wrapped around a body portion (for example, an arm) and be retained in place by a system known in the art, for example, a hook and loop system, a strap and buckle system, or simply a hook disposed at one end of band 114 for engaging fabric or other material in another portion of band 114. FIG. 9D illustrates an embodiment shaped as a shoulder strap 120, the length of which may be adjusted by a buckle 122 and which has coils 124 disposed in one or more points, for example, at the joint between an arm and a shoulder as shown. Each of these embodiments includes one or ore sensors (not shown) that may be coupled to the garment, or that may be applied separately from the garment.

Other embodiments that are not illustrated include, bur are not limited to: a head worn garment, such as a cap; a neck worn garment, such as a neck brace; and a lower-back garment. Each garment and applicator may also utilize the locking, targeting coil feature described previously, without requiring the use of the any sensing components after a proper positioning of the coils in relation to the target nerve or nerves has been established.

Figure 10:
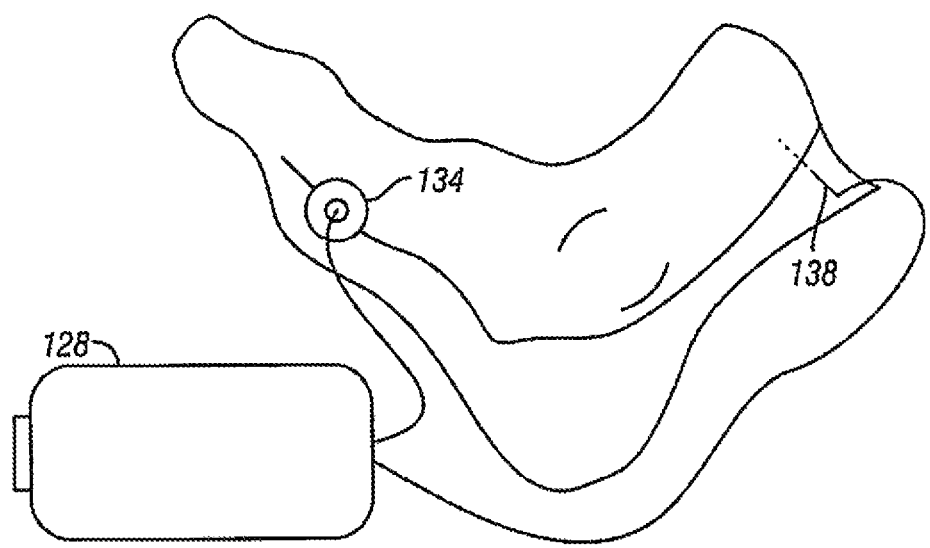
FIG. 10 is a schematic view of an apparatus for providing electrical stimulation.
Figure 11:
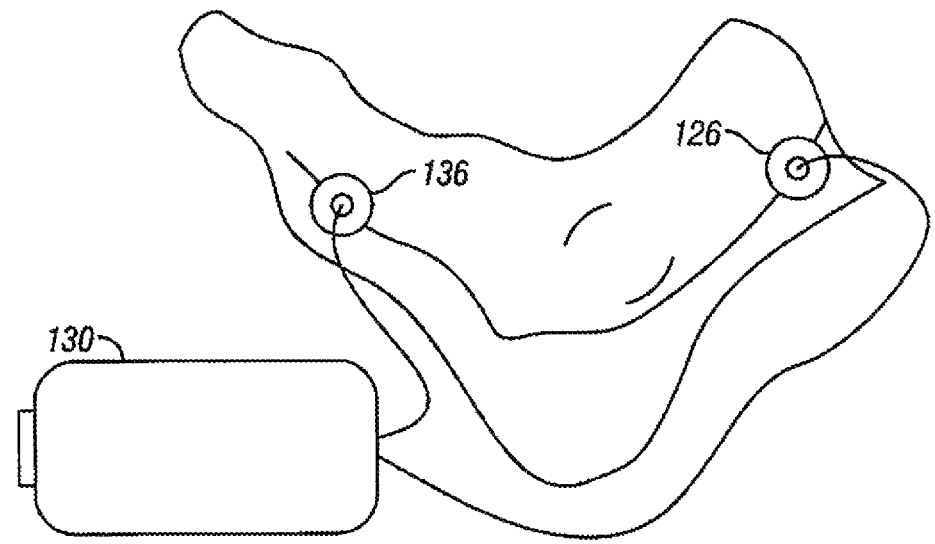
FIG. 11 is a schematic view of another embodiment of an apparatus for providing electrical stimulation.

Still other embodiments are depicted in FIGS. 10 and 11. In these embodiments, the source of energy for nerve stimulation is electrical energy that is dispensed through a percutaneous stimulator, such as a percutaneous needle 124, or a transcutaneous stimulator, such as an electrode 126. As shown in FIG. 10, an electrical pulse controller 128 is electrically connected both to percutaneous needle 124 and to sensor 134, to provide the desired feedback and modulate the power to percutaneous needle 134. In the embodiment of FIG. 11, electrical pulse controller 130 is connected both to electrode 126 and to sensor 136, and performs a function similar to that of electrical pulse controller 128. With these embodiments, nerve conduction may be detected at a site sufficiently distant from the site of stimulation, so to enable detection of nerve conduction despite the confounding interference from the direct electrical stimuli. Further, direct electrical stimulation of nerve and muscle may be tailored to provide optimal therapy and, in the case of electrode migration or other electrode malfunction, to report lack of stimulation of the bodily tissues. Still further, these embodiments enable a reduction in power requirement, because control of the signal is provided by the sensor to the signal generator loop.

As shown, a device constructed according to the principles described herein can provide a targeted and precise stimulation of the posterior tibial nerve, or of other peripheral nerves, in a non-invasive manner by employing an ergonomic wrap or cradle that specifically targets the posterior tibial nerve in a consistent and repeatable manner. For example, in patients with OAB or VI, the novel, reversibly lockable movement of the coils and the use of a logic controller-sensor loop enables the application of a magnetic field that can be varied in location, amplitude and strength according to the amount of stimulation actually induced in one or more target nerves and of the response of the patient to the therapy. An apparatus according to certain embodiments described herein may deliver any frequency of stimulation, including low frequencies, high frequencies, mid frequencies and ultrahigh frequencies, and overlapping and non-overlapping coils may be used to generate the desired field, although overlapping or Helmholtz coils are preferred due to their ability to target a broader region and achieve more thorough stimulation.

Ailments that may be treated through the use of the various embodiments of the apparatus and methods described herein include not only OAB and VI, but also obesity, depression, urinary incontinence, fecal incontinence, hypertension, pain, back pain, restless leg syndrome, Guillain Barre syndrome, quadriplegia, paraplegia, diabetic polyneuropthy, dyskinesias, paresthesias, dental procedure pain, knee osteoarthritis, anesthesia (pain relief during surgery), Alzheimer's disease, angina (chest pain from heart disease), ankylosing spondylitis, back pain, bum pain, cancer pain, chronic pain, dysmenorrhea (painful menstruation), headache, hemiplegia, hemiparesis (paralysis on one side of the body), labor pain, local anesthesia during gallstone lithotripsy, facial pain, trigeminal neuralgia, bruxism (tooth grinding) pain, myofascial pain, pregnancy-related nausea or vomiting, neck and shoulder pain, pain from broken bones, rib fracture or acute trauma, diabetic peripheral neuropathy, phantom limb pain, post-herpetic neuralgia (pain after shingles), postoperative ileus (bowel obstruction), irritable bowel syndrome, postoperative nausea or vomiting, postoperative pain, post-stroke rehabilitation, rheumatoid arthritis, skin ulcers, spinal cord injury, temporomandibular joint pain, detrusor instability, spinal muscular atrophy (in children), pain during hysteroscopy, gastroparesis, chronic obstructive pulmonary disease rehabilitation, carpal tunnel syndrome, soft tissue injury, multiple sclerosis, intermittent claudication, attention-deficit hyperactivity disorder (ADHD), cognitive impairment, knee replacement pain, achalasia, atopic eczema, bursitis, carpal tunnel syndrome, dementia, depression, dry mouth, dystonia, enhanced blood flow in the brain, enhanced blood perfusion of the uterus and placenta, esophageal spasm, fibromyalgia, fracture pain, Guillain-Barre syndrome, hemophilia, herpes, hip pain, interstitial cystitis, irritable bowel syndrome, pruritis, joint pain, labor induction, local anesthesia, menstrual cramps, muscle cramps, muscle spasticity, muscle strain or pain, musculoskeletal trauma, myofascial pain dysfunction syndrome, nerve damage, osteoarthritis, pain medication adjunct, pancreatitis, Raynaud's phenomenon, repetitive strain injuries, sacral pain, schizophrenia, shingles, shoulder subluxation, sickle cell anemia pain, Skin flap ischemia (during plastic surgery), sphincter of Oddi disorders, sports injuries, thrombophlebitis, tinnitus (ringing in the ear), restless legs, tremor, whiplash and neuralgias. In contrast to implantable nerve stimulators, this therapy is completely non-invasive and does not require a major surgery to implant a permanent nerve stimulation device. Moreover, this therapy can be controlled to optimize the level of therapy delivered according to power consumption and nerve stimulation requirements and need not be delivered by a professional healthcare provider.

In other embodiments, neural stimulation may be applied as electrical transcutaneous stimulation, for example, by inserting an invasive electrical needle into a target body part and by modulating stimulation is modulated on the basis of information sent back to the logic controller from the one or more sensors that are used to detect and/or maintain the correct level of stimulation. The transcutaneous electrical stimulation sensor may be placed in the body independently or be incorporated within the wrap and may provide, among other things, feedback as to the quality of the electrical connection to the skin, which is directly related to the bum risk inherently associated with this type of therapy. In fact, these methods of stimulation may not be optimal due to the resulting skin irritation and risk of potential bums, a very serious issue in the large percentage of patients that have neuropathies. Even when patches are applied to monitor transcutaneous stimulation very closely, the patches may still become displaced and allow a bum to occur. Moreover, potentially interfering electrical impulses may develop at the treatment site, creating a noisy environment for the detection of nerve conduction.

In still other embodiments, an external coil or coils may be inductively connected to an implanted coil or coils may be utilized. In these embodiments, an ergonomic applicator may be adjusted by the user or by a healthcare provider such to optimize inductive power transmission between the external and implanted coils. One or more sensors may be utilized to provide a feedback that the relative coil positions have been optimized, and the external coil may then be reversibly locked into position within the ergonomic applicator. Two applications of this embodiment relate to the transfer of power to recharge an implantable device, and to the transfer of power to activate an implantable device.

In the first application, when an implantable rechargeable device is utilized, the external coils may be used for recharging the implanted device by means of inductive fields generated by the external coils. The external coils may include circuitry that determines the amount of resistance encountered by the magnetic field or other electrical properties related to the quality and degree of the magnetic coupling that is being established. Based on this feedback, the position of the external coils may be adjusted manually or automatically to optimize the coupling achieved with during each recharging session. Alternatively, a sensor may be incorporated into the implantable device and may communicate the degree and quality of the magnetic coupling to the external coils and/or the connected circuitry via wireless communication, providing a feedback for the automatic or manual adjustment of the external recharging coils.

The coils within the ergonomic applicator may be reversibly locked into place for the duration of the recharge session, and the implantable device may also communicate to the external recharging unit that the implantable device has been fully recharged, terminating the recharging session has been completed. By providing for an intermittent recharging of an implanted device, an apparatus according to various embodiments described herein can enable the implantable device to devote more power to performing its intended function optimally and with a lesser concern about protecting or extending battery life.

In the second application, the powering coils may contain circuitry to determine the amount of resistance encountered by the applied magnetic field, or other electrical properties that may reflect the quality and degree of the magnetic coupling that is being achieved. Based on this feedback, the powering coils in the applicator may be adjusted manually or automatically to activate and optimize the coil coupling at the beginning of each therapy session. Alternatively, a sensor may be incorporated into the implantable device and communicate the degree and quality of the magnetic coupling externally via wireless communication, which may in turn provide feedback for the automatic or manual adjustment of the powering coil. In one variant of the present embodiment, the inductive coils may be magnetically coupled to a needle targeting the posterior tibial nerve.

An exemplary method of use of an apparatus according to the embodiments described herein on a patient suffering from VI and/or OAB includes the following steps:

The patient places a conductive wrap contained within a flexible material over a region of the ankle (or alternatively over the knee) to provide the required pulsed magnetic field. Alternatively, the patient may use an ergonomic foot/leg rest or cradle having embedded coils.

A sensor (for example, a sensor patch) is placed on the patient's body along the path of the nerve, ideally proximal to the stimulation site to ensure afferent nerve stimulation, and is connected to a logic controller.

A physician or healthcare provider adjusts the coils in the wrap or cradle until nerve conduction is achieved based on patient and sensor feedback. An optimal position is sought, and the coils may be reversibly locked into position within the conductive wrap or ergonomic cradle and remain in this position during subsequent use.

During the therapy session, the logic controller provides an electric current to the coils, generating an inductive magnetic field. In one embodiment, this field begins at low amplitude and slowly ramps up until nerve conduction exceeds a threshold level, as signaled by the sensor and possibly by the patient, who may feel motory conduction. Alternatively, one or more coils may also be activated to increase the covered area of stimulation in the event that stimulation does not occur with the initial coil configuration or is inadequate The optimal stimulation may be determined in a variety of manners, for example, by measuring exposure to electromagnetic fields capable of generating a square wave electric signal at a frequency of 10-30 Hz at the targeted tissue depth. The square wave configuration of the signal may be generated via Fourier transformation or may be a ramped current generated in any manner.

The inductive magnetic pulses continue for an appropriate duration of use, for example, for 15-30 minutes. The sensor may remain in place during the entire therapy session to ensure that stimulation occurs consistently and to provide for appropriate corrections if nerve conduction deteriorated. The logic controller may be powered either by a portable power source such as a battery, or by or a fixed power source such as a traditional wall outlet.

The conductive wrap and/or ergonomic cradle is removed from the body when therapeutic stimulation is not being delivered, typically at the end of the therapy session.

The conductive wrap and/or ergonomic cradle is reapplied along with the sensor patch (ideally disposable) from time to time as indicated, for example, on a daily basis, and steps 4-8 are repeated.

The devices and methods described herein may be applied to any body tissues, including nerve, muscle, skin, vasculature, or any other organ or tissue within the human body. Further, the devices and methods described herein may be used to treat any conditions suited for neuromodulation regardless of whether the stimulation source is an electromagnetic field, a direct electric current, a RF field, infrared energy, visible light, ultraviolet light, ultrasound, or other energy dispensing device.

Figure 12A:
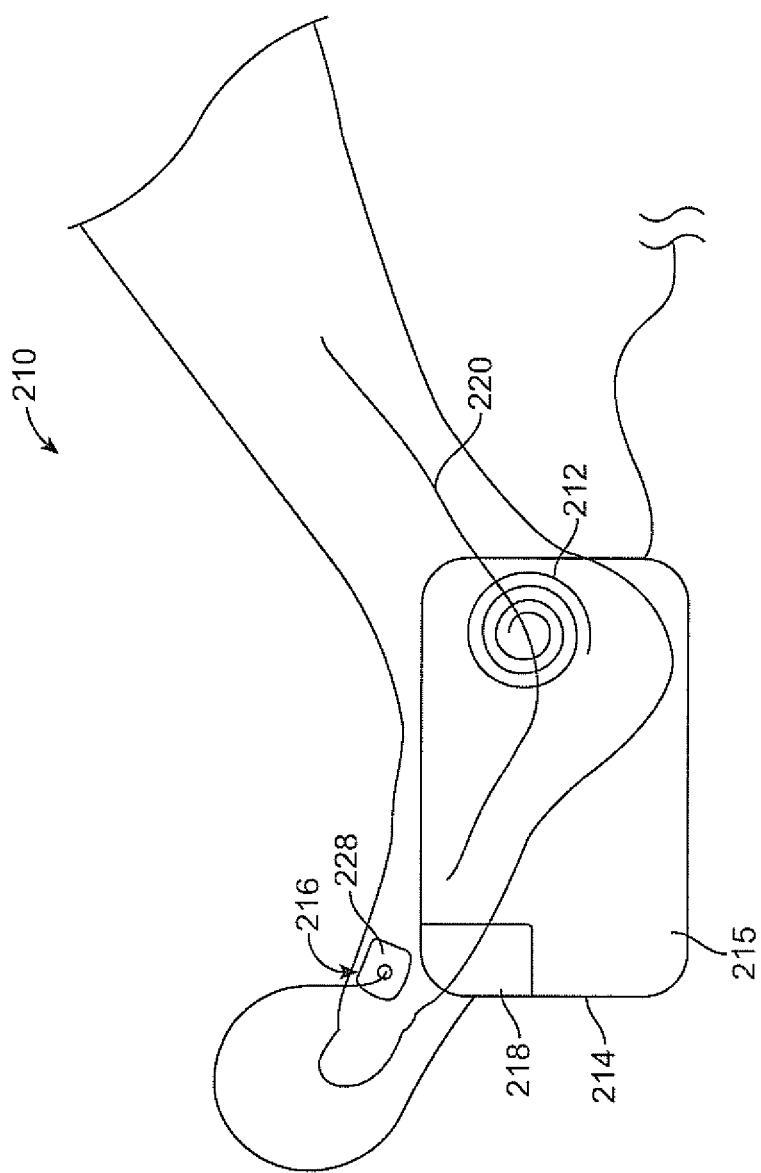
FIG. 12a shows a schematic view of an energy emitting system including a sensor.

In other embodiments, as shown in FIG. 12*a*, an energy emitting system 210 for providing a medical therapy may include one or more conductive coils 212 disposed within or along a housing 214, one or more sensors 216 configured to detect electrical conduction in a target nerve or to detect muscle stimulation, and/or a controller 218 coupled or connected to the conductive coils 212 and optionally in communication with the sensor 216. The coils 212 are configured such that an electrical current generated by the controller 218 is passed through the coils 212 generating a magnetic field which will stimulate a target nerve, e.g., the tibial nerve 220, a muscle or other body part containing a portion of a target nerve, or any nerves branching off of a target nerve, located in proximity to the coils 212. In this particular embodiment, the housing 214 is in the form of a foot cradle, however, the housing could also be in the form of a flexible wrap, garment or other design suitable for use with a subject. In various embodiments described herein, sensors may detect voltage or current and may be connected, coupled, wirelessly connected or coupled or otherwise in communication with the housing and/or controller using a variety of methods or techniques known in the art. The sensor may be placed over a muscle to detect muscle stimulation as a result of stimulating the target nerve (as shown in FIG. 12*a*) or over any other portion of the subject's body suitable for detecting conduction of the target nerve.

In certain embodiments, methods of treating a subject with urinary incontinence or various pelvic floor disorders utilizing the energy emitting systems described herein are contemplated. Symptoms associated with urinary incontinence may be observed, detected, or diagnosed. An energy emitting device having one or more energy generators, e.g., one or more conductive coils or one or more microneedle patches, may be positioned in proximity to a target nerve, e.g., the tibial or posterior tibial nerve or popliteal or sacral nerve or branches thereof of a subject or patient along a first portion of a subject's or patient's body. The subject may or may not be exhibiting symptoms associated with urinary incontinence. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with urinary incontinence, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn may cause the stimulation of a pudendal nerve, sacral plexus, or other nerves in the pelvic floor. Various nerves innervating the various muscles, sphincters, nerves, organs and conduits of the urinary tract and bladder may be stimulated directly or indirectly. In certain embodiments, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of urinary incontinence by achieving the appropriate level of conductance and appropriate level of nerve or muscle stimulation. Appropriate levels for current, frequency, magnetic field, treatment duration, etc., are levels that result in an observed or detected reduction or prevention of symptoms associated with urinary incontinence. Treatment could also be administered and the appropriate levels and parameters achieved through observing or detecting reduction or prevention of symptoms where a sensor is not used. Examples of these symptoms include but are not limited to the inability to control urinary function, urinary leakage, and loss of bladder control.

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat urinary incontinence, the magnetic field or electrical stimulus is applied to a subject or patient until the desired effects (e.g., reduction of symptoms) are achieved.

In certain embodiments, methods of treating a subject with fecal incontinence utilizing the energy emitting systems described herein are contemplated. Symptoms associated with fecal incontinence may be observed, detected, or diagnosed. An energy emitting device having one or more energy generators, e.g., one or more conductive coils or one or more microneedle patches, may be positioned in proximity to a target nerve, e.g., the tibial or posterior tibial nerve, or popliteal or sacral nerve or branches thereof of a subject along a first portion of a subject's body. The subject may or may not be exhibiting symptoms associated with fecal incontinence. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with fecal incontinence, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn causes the stimulation of a pudendal nerve, sacral plexus, or nerves in the pelvic floor. Various nerves innervating the various muscles, sphincters, rectum, nerves, organs and conduits associated with bowel movements, fecal control, and the intestines may be stimulated directly or indirectly. Optionally, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor is in the form a of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the posterior tibial nerve. The current may be adjusted or varied using a controller which is in communication with the energy generator. Adjustments may be made in response to the nerve or muscle stimulation detected by the conductive sensor, in order to optimize or ensure adequate treatment of fecal incontinence by achieving the appropriate level of conductance and appropriate level of nerve or muscle stimulation. Appropriate levels for current, frequency, magnetic field, treatment duration, etc., are levels that result in an observed or detected reduction or prevention of symptoms associated with fecal incontinence. Treatment could also be administered and the appropriate levels and parameters achieved through observing or detecting reduction or prevention of symptoms where a sensor is not used. Examples of these symptoms include but are not limited: the loss of voluntary control to retain stool in the rectum; loss of fecal control; inability to control bowel movements, and fecal leaking:

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat fecal incontinence, the magnetic field or electrical stimulus is applied to a subject or patient until the desired effects (e.g., reduction of symptoms) are achieved.

In certain embodiments, methods of treating a subject with restless leg syndrome utilizing the energy emitting systems described herein are contemplated. Victims afflicted with Restless Leg Syndrome (RLS or Ekbom's syndrome), are unable to remain seated or to stand still. Activities that require maintaining motor rest and limited cognitive stimulation, such as transportation, e.g., in a car, plane, train, etc., or attending longer meetings, lectures, movies or other performances, become difficult if not impossible. These sensations become more severe at night and RLS patients find sleep to be virtually impossible, adding to the diminishing quality of their lives. The urge to move, which increases over periods of rest, can be completely dissipated by movement, such as walking. However, once movement ceases, symptoms return with increased intensity. If an RLS patient is forced to lie still, symptoms will continue to build like a loaded spring and, eventually, the legs will involuntary move, relieving symptoms immediately.

Thus, symptoms associated with restless leg syndrome may be observed, detected, or diagnosed. An energy emitting device having one or more energy generators, e.g., one or more conductive coils or one or more microneedle patches, may be positioned in proximity to a target nerve, e.g., the tibial or posterior tibial nerve, or popliteal or sacral nerve or branches thereof or other nerves associated with restless leg syndrome, of a subject along a first portion of a subject's body. The subject may or may not be exhibiting symptoms associated with restless leg syndrome. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with restless leg syndrome, relative to an energy emitting device such that a target nerve within the first portion of the body is in proximity to at least one energy generator disposed within or along the energy emitting device.

A current is then passed through the energy generator to produce, generate or deliver energy, e.g., a magnetic field or electrical or magnetic energy or stimulus, focused on the tibial or posterior tibial nerve or branches thereof or other nerves associated with restless leg syndrome. This in turn causes the stimulation of a pudendal nerve, sacral plexus or other nerves innervating the various muscles, nerves, or organs associated with restless leg syndrome. The various nerves may be stimulated directly or indirectly. Optionally, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form a of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of restless leg syndrome by achieving the appropriate level of conductance and appropriate level of nerve or muscle stimulation. Appropriate levels for current, frequency, magnetic field, treatment duration, etc., are levels that result in an observed or detected reduction or prevention of symptoms associated with restless leg syndrome. Treatment could also be administered and the appropriate levels and parameters achieved through observing or detecting reduction or prevention of symptoms where a sensor is not used. Examples of these symptoms include but are not limited to: uncomfortable sensations in the limbs, irresistible urges to move, usually the legs; motor restlessness; when at rest, symptoms return or worsen; and symptoms worsen in the evening and at night.

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat restless leg syndrome, the magnetic field or electrical stimulus is applied to a subject or patient until the desired effects (e.g., reduction of symptoms) are achieved.

In certain embodiments, methods of treating a subject suffering from premature ejaculation or various pelvic floor disorders utilizing the energy emitting systems described herein are contemplated. Symptoms associated with premature ejaculation may be observed, detected, or diagnosed. An energy emitting device having one or more energy generators, e.g., one or more conductive coils or one or more microneedle patches, may be positioned in proximity to a target nerve, e.g., the tibial or posterior tibial nerve or popliteal or sacral nerve or branches thereof of a subject along a first portion of a subject's body. The subject may or may not be exhibiting symptoms associated with premature ejaculation. In the case of the conductive coils, the coils may be positioned within or along a housing, such as a foot or knee cradle, and a foot or leg may be positioned therein. In the case of a microneedle patch, the patch may be attached to a subject's skin. Optionally, the method involves positioning a first portion of a subject's body, the subject exhibiting symptoms associated with premature ejaculation, relative to an energy emitting device such that a target nerve within the first portion of the body is in proximity to at least one energy generator disposed within or along the energy emitting device.

A current is then passed through the energy generator to produce, generate or deliver energy, e.g., a magnetic or electromagnetic field or electrical or magnetic energy or stimulus, focused on the tibial or posterior tibial nerve or branches thereof. This in turn may cause the stimulation of a pudendal nerve, sacral plexus, or other nerves in the pelvic floor or nerves associated with the control of ejaculation. Various nerves innervating the various muscles, sphincters, nerves, organs and conduits of the urinary tract, bladder or reproductive system, or pelvic floor may be stimulated directly or indirectly. Optionally, a current is passed through one more coils, which generates a magnetic or electromagnetic field which stimulates the posterior tibial nerve. In certain embodiments, the positioning of the coils relative to the first portion of the subject's body may be adjusted to re-focus the magnetic field on the posterior tibial nerve as needed. In certain embodiments, a current is passed through a microneedle patch generating or delivering an electrical or magnetic stimulus or field. The positioning of the microneedle patch relative to the first portion of the subject's body may be adjusted to re-focus the electrical or magnetic stimulus or field on the posterior tibial nerve as needed.

Optionally, electrical conduction through the target nerve, e.g., the posterior tibial nerve, or muscle stimulation can be detected via at least one sensor. A conductive sensor may be positioned in proximity to the posterior tibial nerve along a second portion of the subject's body. Optionally, a sensor may be positioned over a corresponding muscle to detect muscle stimulation or twitching resulting from nerve stimulation. Optionally, the electrical conduction is detected along a second portion of the subject's body which is different from the first portion of the body. Optionally, the sensor in the form of a microneedle patch. In certain embodiments, the sensor may be positioned behind a subject's knee to detect the electrical conduction along the afferent posterior tibial nerve or on another portion of a patient's leg or foot. In other embodiments, the sensor may be positioned within or along a housing along with the one or more conductive coils.

Where a sensor is used, a signal is received from the sensors and the signal is indicative of the electrical conduction of the target nerve, e.g., posterior tibial nerve. The current may be adjusted or varied using a controller which is in communication with the energy generator. Adjustments may be made in response to the nerve or muscle stimulation detected by the conductive sensor, in order to optimize or ensure adequate treatment of premature ejaculation by achieving the appropriate level of conductance and appropriate level of nerve or muscle stimulation. Appropriate levels for current, frequency, magnetic field, treatment duration, etc., are levels that result in an observed or detected reduction or prevention of symptoms associated with premature ejaculation. Treatment could also be administered and the appropriate levels and parameters achieved through observing or detecting reduction or prevention of symptoms where a sensor is not used. Examples of these symptoms include but are not limited to: ejaculation that frequently occurs within one minute or less of penetration; the inability to delay ejaculation on penetrations; or persistent or recurrent ejaculation with minimal stimulation before, on or shortly after penetration.

In certain embodiments, the amplitude, frequency, direction of a generated magnetic field, electrical or magnetic stimulus, or firing sequence of the coils or microneedles making up the microneedle array may be adjusted. Optionally, the current may be varied according to a muscular response in the patient. Thus, to treat premature ejaculation, the magnetic field or electrical stimulus is applied to a subject or patient until the desired effects (e.g., reduction of symptoms) are achieved.

Exemplary treatment parameters for treating various conditions, e.g., urinary incontinence, using the systems and methods described herein may include the following. Operation of a conductive coil at about 10 to 20 hertz generating a magnetic field of about 0.25 to 1.5 tesla, where the coil is administered to a patient for a duration of about 30 minutes/day or 30 minutes per week, depending on the severity of the symptoms, until the symptoms subside. The above treatment parameters or variations on the parameters may be used for treatment of urinary incontinence, fecal incontinence, restless leg syndrome, or premature ejaculation or other conditions. For example, the coil may be operated at various parameter ranges falling with the following ranges: about 5 to 100 hertz, about 1 to 10 tesla, for about 15 minutes to 2 hours per day or week. In treating premature ejaculation, a patient may receive treatment about 4 to 10 hours prior to intercourse. A maintenance phase of treatment, after the initial treatment, may vary for various conditions. For example, the maintenance phase may require application of the systems and methods described herein at the parameters described herein for 30 minutes/week or 30 minutes/month. Any treatment parameter may be varied or modified based on the effect on the patient or sensor or patient feedback regarding stimulation, until the desired result of treating or preventing a condition is achieved.

In certain embodiments, the energy emitting device, e.g., foot cradle, knee cradle, etc., includes a conductive coil positioned such that a target nerve is automatically targeted. The conductive coil is configured, sized and positioned within the device such that the generated electromagnetic or magnetic field may encompass and stimulate the target nerve in any patient based on the target nerve's anatomical location, thus providing automatic targeting of the nerve in any patient once the patient positions a particular body portion in the device.

In various embodiments described herein, sensors may detect voltage or current and may be connected, coupled, wirelessly connected or coupled or otherwise in communication with housing, conductive coils, microneedle patch, energy emitting apparatus or device, energy generators, or electrode needles and/or controller using a variety of methods or techniques known in the art. In various embodiments described herein, housings, conductive coils, microneedle patches, energy emitting apparatus, energy generators, or electrode needles may be connected, coupled, wirelessly connected or coupled or otherwise in communication with each other, controllers or sensors, using a variety of methods or techniques known in the art.

An energy emitting system for providing a medical therapy according to any of the embodiments described herein may include an energy emitting device and/or one or more energy generators for generating an electromagnetic field or magnetic field and/or delivering an electromagnetic stimulus. In certain embodiments, the energy generator may be a conductive coil, which is configured to generate an electromagnetic or magnetic field to be focused on a target nerve. The one or more conductive coils are optionally positioned within or along a housing, as described herein. Various embodiments of conductive coils are contemplated. A conductive coil utilized in any of the embodiments described herein may optionally include a variety of configurations or features, e.g., cooling features for conduction or convection cooling, which optimize the conductive coil's effectiveness in generating a magnetic field and stimulating a target nerve, while providing a safe and effective medical therapy for a patient.

The conductive coils described herein may have a variety of dimensions, shapes, and sizes. The diameter of the central aperture of a coil may vary. For example, the diameter may range from about 0.5 inch to 2 inches or 1 inch to 1.5 inches or the aperture may have a diameter of about 1 inch. The diameter of the coil body may vary. For example, the diameter may range from about 3.0 to about 7 inches or from about 4 to about 5 inches or the diameter may be about 4.5 inches. The coil body may include any suitable number of turns. For example, the coil body may include from about 2 to about 25 turns or from about 10 to about 20 turns or 14 to 17 turns. A turn may have various dimensions. For example, the turn or end or cross section of the turn may have a height that is greater than its width or thickness, e.g., 15 to 60 times or 25 to 50 times greater in height relative to its width. In certain embodiments, a turn or an end or cross section of a turn may have a height ranging from about 1 to 5 cm or from about 10 mm to 51 mm (about 0.3 inches to 2 inches) or about 25 mm to 40 mm (about 1 inch to 1.5 inches) or about 12 mm to 40 mm (about 0.5 inch to 1.5 inch) or about 0.5 inch to 2 inch. The turn or end or cross section of the turn may have a width ranging from about 0.5 mm to about 5 mm (about 0.019 inch to 0.19 inch) or from about 1 mm to about 2 mm (about 0.03 inch to 0.07 inch) or about 0.2 mm to about 1.6 mm (about 0.01 inch to 0.06 inch). Optionally, the dimensions may allow the coil turns to be tightly packed or rolled while still maintaining gaps or spaces in between adjacent turns, allowing for conduction and/or cooling. Optionally, the dimensions may allow the coil to be more loosely packed or rolled, allowing for conduction and/or cooling. The above are exemplary dimensions, where other dimensions are also contemplated depending on the use and configuration of a device.

In certain embodiments, a turn or end or cross section of a turn may have a height ranging from about 1 to 5 cm or from about 10 mm to 51 mm (about 0.3 inches to 2 inches) or about 25 mm to 40 mm (about 1 inch to 1.5 inches) or about 12 mm to 40 mm (about 0.5 inch to 1.5 inch) or about 0.5 inch to 2 inch. The turn or end or cross section of the turn may have a width ranging from about 0.5 mm to about 5 mm (about 0.019 inch to 0.19 inch) or from about 1 mm to about 2 mm (about 0.03 inch to 0.07 inch) or about 0.2 mm to about 1.6 mm (about 0.01 inch to 0.06 inch). The dimensions may allow the coil turns to be tightly packed or rolled while still maintaining gaps or spaces in between adjacent turns, allowing for conduction and/or cooling. The conductive coil may have a diameter ranging from about 4.5 inches to about 5 inches. In certain embodiments, the number of turns of a conductive coil can vary, e.g., a coil may include from about 14 to 20 turns, where a gap separates all or many of the turns from an adjacent turn.

Any of the embodiments of coils described herein and illustrated in the corresponding figures may have the above dimensions and configurations or any other suitable dimension or configuration depending on the coils intended use.

In any of the conductive coil embodiments described herein, the first turn of a conductive coil may optionally surround a central aperture which is sized to receive a first portion of a patient's body such that the conductive coil is positioned in proximity to the underlying target nerve. The central aperture also aids in the cooling process as air or other fluid can pass through the aperture, over and around the conductive coil surface. Optionally, the central aperture may be sized to surround at least a portion of a malleolus or other body portion, such that the conductive coil is positioned in proximity to the tibial nerve. As described supra, the conductive coils may be in the form of a spiral that is substantially planar, substantially conical or other configurations best suited for a particular device or patient.

Coils used in any of the embodiments described above and illustrated in the corresponding figures may take on a variety of shapes, sizes, and configurations. For example, a coil may be shaped as a spiral (as shown) or have a simple helical pattern or be a figure eight coil, a four leaf clover coil, a Helmholtz coil, a modified Helmholtz coil, or may be shaped as a combination of the aforementioned coil patterns. Additionally, other coil designs beyond those mentioned hereinabove might be utilized as long as a magnetic field is developed that will encompass a target nerve.

Optionally, any of the conductive coils described herein can be coated or otherwise covered with a material, e.g., a non-electrically conductive material, to ensure that the conductive surface of the turns making up the coil do not come into contact with each other.

In any of the above embodiments, the system may optionally include a sensor, e.g., a laser Doppler or ultrasound Doppler. The sensor may be used to detect (e.g., through the openings or spaces in the coil) the positioning of the tibial artery which runs along the tibial nerve, to help ensure proper placement of the patient's body relative to the conductive coil in order to conduct magnetic induction therapy.

It is also contemplated that any of the energy emitting systems or devices described herein can be used with or without a sensor for detecting conduction of a stimulated nerve or muscle stimulation resulting from the magnetic field generated by the conductive coil and delivered to a patient or an electrical stimulus delivered to a patient. Also, in any of the above embodiments, a controller may optionally be connected, coupled, integral to or otherwise in communication with the conductive coils and/or the sensor. Optionally, the sensor may be connected, coupled, integral to or otherwise in communication with the conductive coil.

Figure 12B:
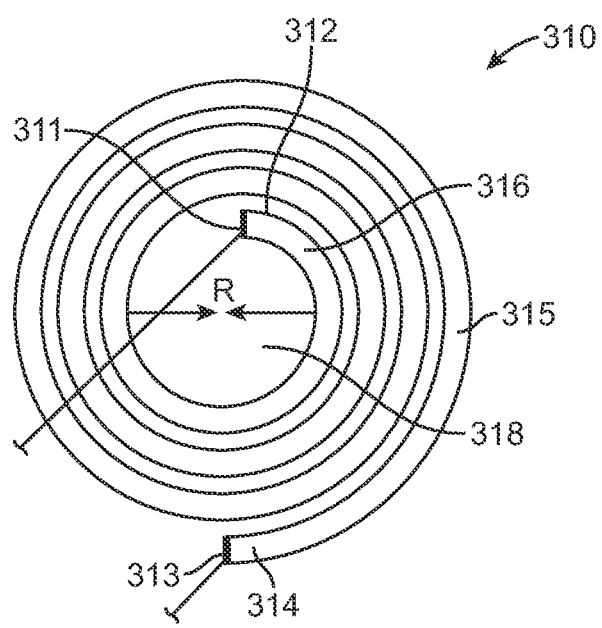
FIG. 12b shows a side view of a variation of a conductive coil.

Energy emitting systems described herein may include a variety of conductive coils. In certain embodiments, a conductive coil 310 (as shown in FIG. 12b) is provided which includes a first end 312, a second end 314, and one or more turns 315 extending there between. The ends of the coil include electrical contact points 311, 313. A first turn 316 surrounds a central aperture 318 which is sized to receive a portion of a patient's body such that the conductive coil can be positioned in proximity to an underlying target nerve. One or more second turns 315 surrounding the first turn 316 may have a radius or radius of curvature greater than the radius or radius of curvature of the first turn.

Figure 12C:
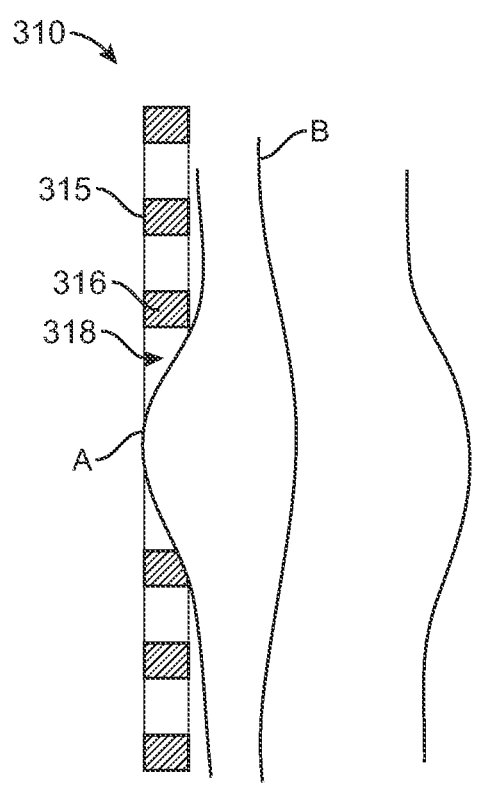
FIG. 12c shows a cross sectional view of the conductive coil of FIG. 12b positioned on a patient.

FIG. 12c shows a cross section of coil 310 positioned on a patient. The central aperture 318 may be sized or configured to surround a portion of a patient's body, for example, at least a portion of a malleolus A. The radius of the central aperture 318 has a length sufficient to allow the central aperture 318 to surround at least a portion of malleolus A, such that the conductive coil can be positioned in closer proximity to the underlying tibial nerve B. As a result, the electromagnetic flux generated by the conductive coil is concentrated or substantially concentrated on the target nerve, e.g., the tibial nerve, thereby maximizing conduction of the target nerve by the electromagnetic or magnetic field generated by the coil. Examples of suitable radius lengths include but are not limited to a radius having a length from about 1 cm to 20 cm or from about 2 cm to about 10 cm or from about 2 cm to about 5 cm. The radius length may vary and/or be adjustable depending on the anatomy of a particular patient in order to accommodate the patient's anatomy and provide efficient conduction of a target nerve. The coil may be adjustable or in certain embodiments it may be fixed or pre-sized or not adjustable.

Figure 13A:
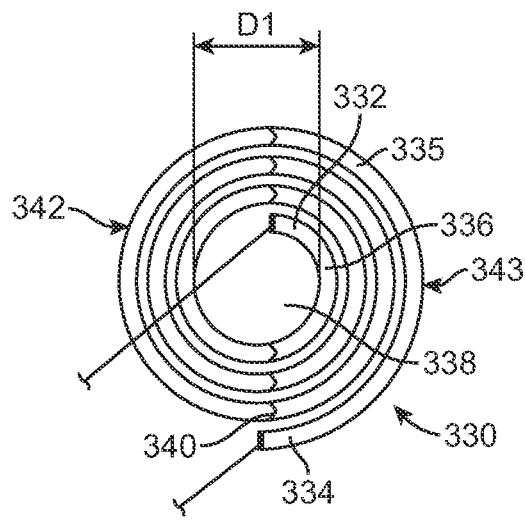
FIG. 13a shows a side view of a variation of a conductive coil.

Referring to FIG. 13a, in certain embodiments, an energy emitting system may include an adjustable, movable or manipulatable conductive coil 330 configured to accommodate the anatomy of a patient and to generate an electromagnetic or magnetic field focused on a target nerve. The conductive coil 330 may have a first end 332, a second end 34, and one or more turns 335 extending there between. A first turn 336 surrounds a central aperture 338, wherein the central aperture 338 is adjustable or movable between at least a first configuration and a second configuration, the second configuration having a radius that is greater than a radius of the first configuration, such that the conductive coil can accommodate, conform to, surround or be positioned or fit around or on an anatomical structure of a patient and thereby be positioned in proximity to the underlying target nerve.

In certain embodiments, the central aperture 338 is adjustable and/or movable or can be manipulated from a first configuration to a second configuration or between various non-expanded, expanded and contracted configurations such that the conductive coil 330 may be conformed, adjusted or fit onto or around or positioned onto or around or accommodate an anatomical structure of a patient, thereby allowing the conductive coil 330 to be positioned in proximity to an underlying target nerve. The adjustable conductive coil 330 may be expanded and/or contracted to adjust or vary the dimensions of the coil or the central aperture 338, increasing and/or decreasing the diameter or radius of the coil or central aperture 338 to accommodate the anatomy of a patient or to be positioned or fit around or over an anatomical structure of a patient.

Figure 13B:
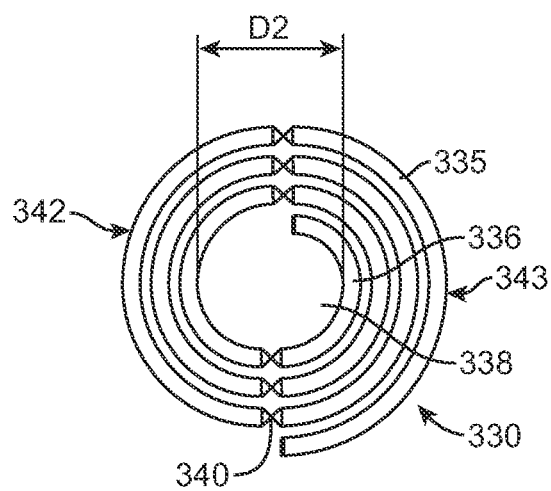
FIG. 13b shows a side view of the conductive coil of FIG. 13a with the central aperture in an expanded configuration.
Figure 13C:
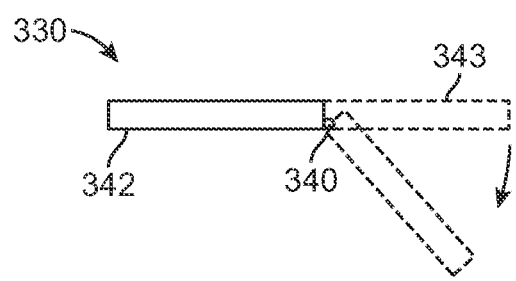

In certain embodiments, as shown in FIGS. 13a-13c, the adjustable conductive coil 30 may include a pivot or hinge 340 positioned along a central axis of the conductive coil 330. The hinge 340 may be positioned on one or more turns 336 of the coil. In certain embodiments, a hinge is positioned on each turn 335 of the coil, along a central axis of the coil. The hinge 340 defines a coil first portion 342 and a coil second portion 343 and the coil first portion 342 and/or coil second portion 343 may be pivotable about the hinge 340. By pivoting the coil first portion 342, the coil second portion 343, or both, the radius or diameter of central aperture 338 may be expanded, thereby expanding the conductive coil 330. The coil may be pivoted in a manner that reduces or contracts the central aperture from an expanded configuration.

For example, as shown in FIGS. 13a and 13b, the diameter of the central aperture may be adjusted such that it is increased from diameter D1 to an expanded diameter D2 when the coil 330 is expanded by pivoting or rotating coil first portion 342 and/or coil second portion 343 about hinge 340. By pivoting or rotating coil first portion 342 and/or coil second portion 343 about hinge 340, the diameter D2 of central aperture 338 can be expanded relative to the diameter D1 of central aperture 338 and/or contracted to return the coil 330 to a closed configuration, e.g., after placement.

FIG. 13c shows a side view of the conductive coil 30, where coil second portion 343 is rotatable or pivotable about a hinge 340 in order to adjust the diameter or radius of the coil and/or the diameter or radius of the central aperture.

Any suitable mechanism known in the art for providing pivoting or rotational movement such that the portions of the coil or the coil turns may pivot or rotate relative to one another such that the coil can be positioned or fit into place on a patient may be utilized in the embodiments described herein.

Figure 13D:
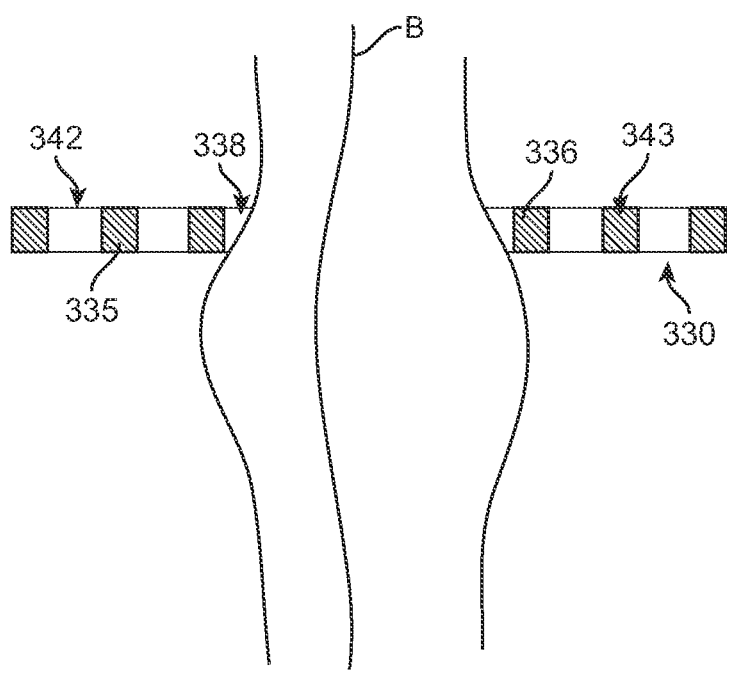
FIG. 13d shows a cross sectional view of the conductive coil of FIG. 13a positioned on a patient.

As shown in FIG. 13d, which is a cross sectional view of coil 330 positioned around a patient's leg, adjusting or manipulating the central aperture 338, e.g., by expanding, contracting, enlarging, or reducing the size of the central aperture 338, allows the conductive coil 330 to be positioned or advanced over a first portion of a patient's body, for example a patient's foot, such that the coil can be placed around or in proximity to a second portion of a patient's body, for example, an ankle or leg, and therefore, positioned in close proximity to an underlying target nerve, e.g., the tibial nerve B. Such placement and positioning helps focus or concentrate the electromagnetic flux delivered by the coil on the target nerve and maximize conductance of the nerve and the effectiveness of the electromagnetic therapy. The adjustable nature of the coil allows the coil to accommodated differing anatomy and body portion sizes and shapes of different patients.

Figure 14A:
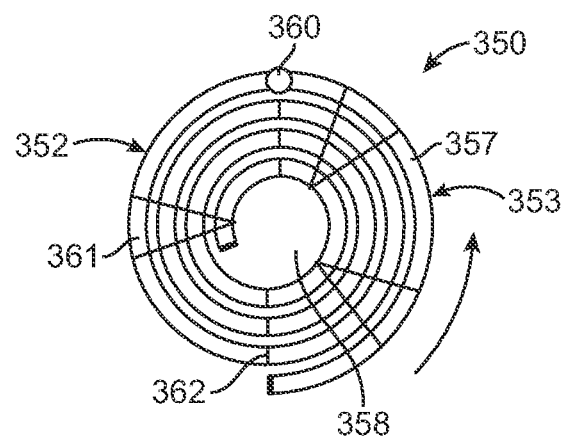
FIG. 14a shows a side view of a variation of a conductive coil.
Figure 14B:
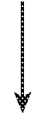
FIG. 14b shows a side view of the conductive coil of FIG. 14a with the central aperture in an expanded configuration.
Figure 14B:
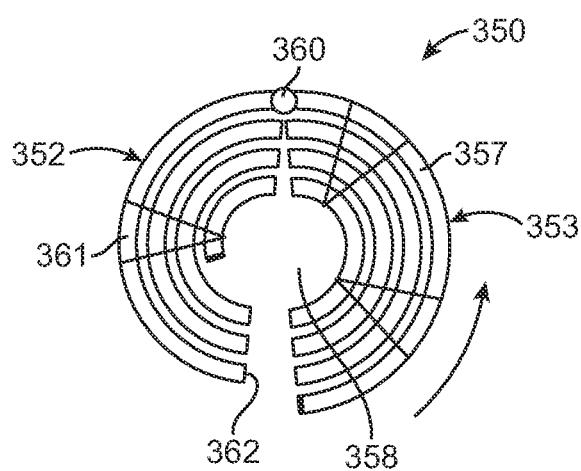

As shown in FIGS. 14a and 14b, another embodiment of an adjustable conductive coil 350 is provided. Conductive coil 350 includes a pivot or hinge 360 positioned on the outer most turn 357 of the conductive coil 350. Optionally, a non-conductive material may be used to connect adjacent turns to one another to maintain separation between adjacent turns as the coil and central aperture 358 are adjusted and coil first portion 352 and/or coil second portion 353 are rotated relative to one another. For example, the non-conductive material may be in the form of a wedge 361 (e.g., an epoxy wedge) attached to the surfaces and/or around conductive coil 350. Additionally, each of the turns may include a break 362 or separation along a central axis of the coil and in line with the pivot or hinge 360, which separates the coil 350 into coil first portion 352 and a coil second portion 353.

In use, coil first portion 352 and/or coil second portion 353 may be rotated or pivoted about hinge 360, thereby separating the first and second portions 352, 353 from one another and expanding the central aperture 358, as shown in FIG. 14b. Expansion of the coil 350 allows the coil to be fit or positioned around a portion of a patient's body, e.g., a leg or ankle, like a bracelet, such that the coil can be placed in close proximity to the underlying target nerve, and the electromagnetic or magnetic flux generated by the coil can be concentrated on the target nerve.

In certain embodiments, in order to maintain electrical current flow through the coil turns and portions of an expandable coil and to minimize energy loss, a variety of contacts, couplers or connecting features may be implemented on portions of a conductive coil. For example, in certain embodiments, the interface between a coil first portion and coil second portion may include an electrically conductive material forming a contact or coupler. The contacts may be positioned on the first and/or second coil portions or on the interface between the first and/or second portions, such that when the first and second coil portions are reconnected after being positioned on a patient, the electrical current conducted through the coil is uninterrupted and flows through the conductive coil without substantial current or energy loss, in order to generate an electromagnetic or magnetic field.

In certain embodiments, female and male interconnecting members may be provided on the first and/or second coil portions along a central axis of the adjustable conductive coil in order to connect or hold the first and second coil portions together. For example, a coil first portion may include a female member for receiving a male member positioned on the coil second portion, thereby providing a secure coupling or electrical connection between the first and second coil portions to maintain electrical current flow through and between the first and second conductive coil portions and to prevent interruption of electrical current flow between the first and second coil portions.

Figure 15A:
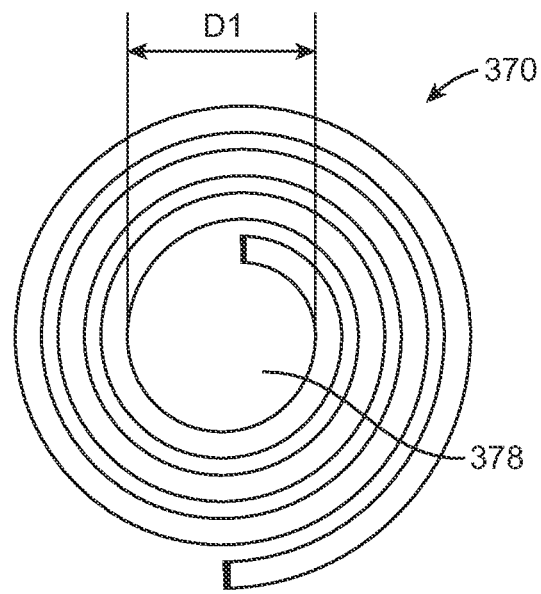
FIG. 15a shows a side view of a variation of a conductive coil.
Figure 15B:
FIG. 15b shows a side view of the conductive coil of FIG. 15a with the central aperture in an expanded configuration.
Figure 15B:
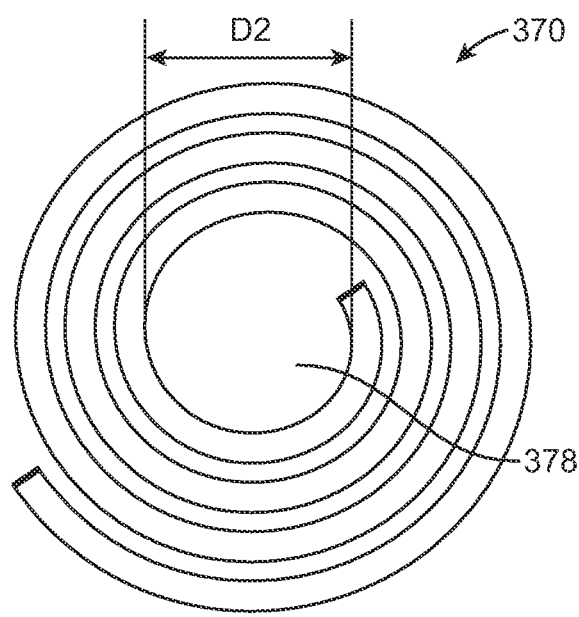

In certain embodiments, as shown in FIGS. 15a & 15b, an adjustable conductive coil 370 may be expanded by unraveling or loosening the conductive coil 370 such that the diameter or radius of the central aperture 378 of the conductive coil 370 is increased from diameter D1 (shown in FIG. 15a) to an expanded diameter D2 (shown in FIG. 15b). The conductive coil may include a variety of materials which provide flexibility, are bendable, or have shape memory properties. Examples of such materials include but are not limited to, nitinol, copper, and other conductive materials. The conductive coil 370 may be unraveled to expand the central aperture 378 and/or contracted or tightened to reduce the size of the central aperture in order to accommodate, surround, be positioned on, or conform to the anatomy of a patient, thereby permitting positioning of the conductive coil in close proximity to the underlying target nerve.

Figure 16A:
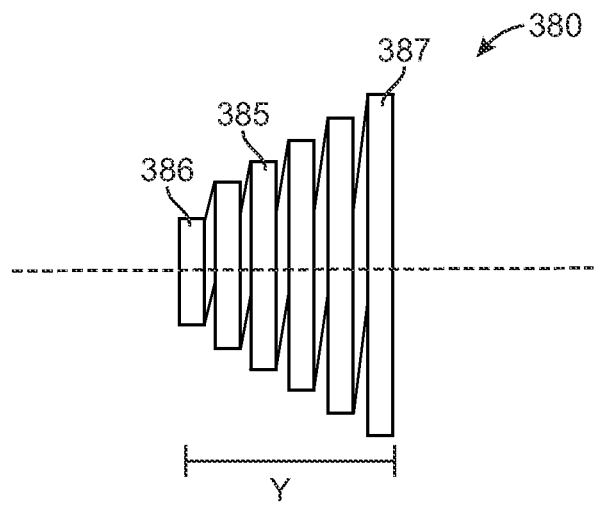
FIG. 16a shows an end view of a variation of conductive coil.
Figure 16B:
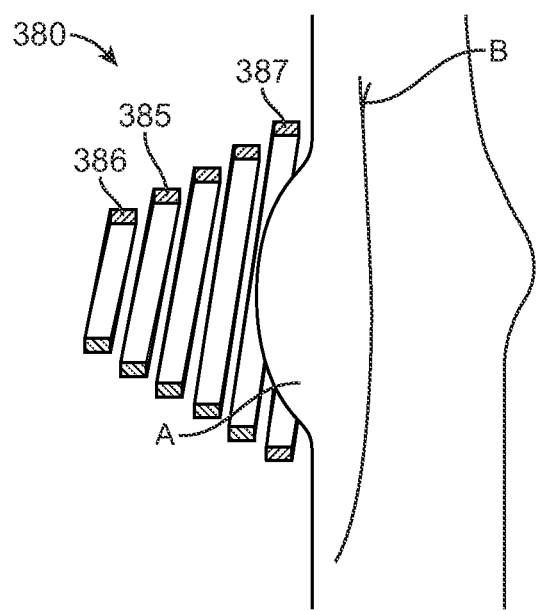
FIG. 16b shows a cross sectional view of the conductive coil of FIG. 16a positioned on a patient.

In another embodiment of a conductive coil, referring to FIGS. 16a-16b, the conductive coil 380 may have a substantially conical configuration or shape. In a conically configured coil, as shown in FIG. 16a, the center of the conductive coil 380, starting with inner turn 386, is positioned a distance Y from outer turn 387, along the longitudinal axis (shown as dashed line) of the coil. Each successive turn 385 may extend beyond the perimeter or circumference of the adjacent larger turn 385 along the longitudinal axis of the coil.

FIG. 16b shows a cross sectional side view of the conductive coil 380, having a conical configuration. In use, the conductive coil 380 may be positioned against, over or around a portion of a patient's body, for example, a leg, over at least a portion of a patient's malleolus A or ankle and thereby in close proximity to the underlying target nerve B, e.g., a tibial nerve.

In certain embodiments, the conductive coil 380 may be adjusted by either increasing or decreasing the distance Y between the inner and outer turns 386, 387. Depending on the anatomy of a patient, the inner turn 386 may be pushed or advanced a distance Y away from the outer turn 387, such that the conductive coil 380 expands into a cone shape, which can be placed over and/or around a portion of a patient's body, for example, a malleolus A. Thus, the varying diameters of the successive turns 385 from the inner to the outer turns 386, 387 allow the coil to accommodate, surround, be positioned on, or conform to varying sizes of portions of a patient's body, allowing the coil 380 to be positioned in close proximity to an underlying target nerve. The conductive coil 380 may include a variety of materials which provide flexibility, are bendable, or have shape memory properties. Examples of such materials include but are not limited to, nitinol, copper, and other conductive materials. Additionally, the conductive coil 380 may include any of the pivoting or rotational mechanism discussed herein to provide for expansion or contraction of the conductive coil, any of the turns of the coil, or the central aperture of the coil.

In certain embodiments, methods of electromagnetic or magnetic induction therapy utilizing the various adjustable conductive coil configurations described herein, which accommodate varying anatomy of patients and allow for improved positioning of a conductive coil in close proximity to a target nerve are provided. The methods may include positioning a conductive coil relative to a first portion of a patient's body in proximity to an underlying target nerve such that the electromagnetic flux generated by the conductive coil can be concentrated or focused on the underlying target nerve. The conductive coil or a central aperture of the conductive coil may be adjusted, such that the conductive coil is expanded or contracted in order to surround, be positioned on, conform to, accommodate, approximate or receive the first portion of the patient's body. Once in position or during positioning of the coil, an electrical current can be passed or conducted through the conductive coil to generate an electromagnetic or magnetic field focused on the target nerve for stimulating the target nerve.

In certain embodiments, adjusting a conductive coil may involve expanding a central aperture of the conductive coil to surround a first portion of a patient's body to position the conductive coil in close proximity to the underlying nerve. In certain embodiments, adjusting a conductive coil may involve contracting a central aperture of the conductive coil to surround a first portion of a patient's body to position the conductive coil in close proximity to the underlying nerve. Expansion or contraction of an adjustable conductive coil may be performed by a variety of mechanisms as described herein. Examples include but are not limited to pivoting a first and or second portion of a conductive coil about a hinge, unraveling or tightening the conductive coil to increase or decrease the radius or diameter of the central aperture and/or one or more turns making up the conductive coil.

An adjustable coil may include an expandable central aperture that can be advanced over a second portion of the patient's body to position the conductive coil in proximity to a first portion of the patient's body. For example, the adjustable features of a coil may allow the coil to expand to a sufficient size or diameter to fit over or around a patient's foot such that the coil may be advanced and positioned around the patient's leg or ankle. Once in position, the coil can be contracted or further adjusted, as necessary, to snuggly or closely fit around a patient's leg and in close proximity to the underlying target nerve, e.g., the tibial nerve.

Optionally, a sensor configured to detect electrical conduction of the target nerve may be utilized and a controller may be coupled to or in communication with the coil and/or the sensor (not shown), as described in various embodiments herein.

A coil can take on a variety of configurations depending on the materials used to construct the coil and the particular use of a coil. For example, a coil may be substantially planar in certain embodiments. In other embodiments, a coil may be substantially conical or the coil may be in the shape of solenoid.

In certain embodiments, an energy emitting system for providing a medical therapy comprises a conductive coil configured to generate an electromagnetic or magnetic field focused on a target nerve, the conductive coil having a first end, a second end, and a first turn there between, the first turn surrounding a central aperture; wherein the central aperture can be manipulated or is movable between a first configuration and a second configuration, the second configuration having a radius that is greater than a radius of the first configuration, such that the conductive coil can accommodate an anatomical structure of a patient and/or be positioned in proximity to the underlying target nerve.

The conductive coil further may comprise a hinge positioned along a central axis of the conductive coil, the hinge defining a coil first portion and a coil second portion, wherein the coil first portion or coil second portion are pivotable about the hinge such that dimensions of the central aperture can be manipulated or altered or enlarged or reduced. The central aperture may be expandable from non-expanded configuration to an expanded configuration such that the conductive coil can conform to an anatomical structure of a patient and/or be positioned in proximity to the underlying target nerve.

The central aperture may have a radius with a length from about 1 cm to 10 cm or from about 2 cm to about 5 cm in length. The interface between the coil first portion and coil second portion may comprise an electrical coupling contact. The coil first portion may have a male member and a coil second portion may have a female member for receiving the male member, such that the coil first and second portions connect to maintain electrical coupling.

The central aperture may be movable or can be manipulated such that the conductive coil can be positioned around a patient's leg in proximity to the underlying target nerve. The central aperture may be movable or can be manipulated such that the conductive coil can be positioned around a patient's ankle in proximity to the underlying target nerve. The central aperture may be movable or can be manipulated such that the conductive coil can be positioned around at least a portion of a patient's malleolus in proximity to the underlying tibial nerve.

In certain variations, an energy emitting system may include a sensor configured to detect muscle stimulation or electrical conduction of a target nerve or to detect stimulation of a nerve, muscle or other body tissue. A controller may be provided which is coupled to the coil and in communication with the sensor.

In certain embodiments, a method of magnetic induction therapy comprises: positioning a conductive coil relative to a first portion of a patient's body in proximity to an underlying target nerve to concentrate an electromagnetic flux on the underlying target nerve, wherein positioning comprises altering, moving, enlarging, reducing, adjusting or manipulating a central aperture of the conductive coil or the coil, such that the conductive coil can accommodate, approximate or receive the first portion of the patient's body; and passing a current through the conductive coil to generate an electromagnetic or magnetic field focused on the target nerve.

The central aperture of the conductive coil may be expanded to surround a first portion of a patient's body such that the conductive coil can be positioned in proximity to the underlying nerve. The central aperture of the conductive coil may be contracted to surround a first portion of a patient's body such that the conductive coil can be positioned in proximity to the underlying nerve. The altering, moving, enlarging, reducing, adjusting or manipulating of the central aperture may comprise pivoting a first portion of a conductive coil about a hinge or it may comprises unraveling the conductive coil or it may comprise tightening the conductive coil. The central aperture of the conductive coil may be advanced over a second portion of the patient's body to position the conductive coil in proximity to the first portion of the patient's body.

In any of the embodiments described herein, the central aperture or coil, e.g., the shape, dimensions, size, orientation, or configuration of the coil, or any portion of the coil, e.g., the central aperture or other turns of the coil, may be altered, adjusted, manipulated, moved, expanded, enlarged, reduced, or contracted temporarily, permanently or interchangeably in order to position or maneuver the coil or energy emitting system and/or position the coil relative to a body or body part.

The variations of conductive coils described herein are configured or designed in a manner that allows for positioning of a coil in close proximity to a target nerve, muscle or other body tissue to be stimulated. The ability to position the coil in close proximity to the target stimulation site allows the energy emitting systems or devices for performing electromagnetic therapy to operate at lower power levels, which may result in a reduction of energy requirements, noise and costs associated with the systems or devices described herein.

In certain variations, an energy emitting system may include a sensor for detecting the position of patient's body part relative to a conductive coil or vice versa, to determine whether or ensure that a patient's body or body part is properly positioned or correctly located in proximity to a conductive coil or to determine whether or ensure that the conductive coil is properly positioned or correctly located in proximity to a patient's body or body part for effective electromagnetic stimulation or therapy. The positioning of the patient's body part or the positioning of the conductive coil may be adjusted based on feedback provided by the sensor regarding the relative position of the system or coil and the patient's body part. The sensor may be positioned anywhere on an applicator, housing, or coil of the system. Various sensors may be utilized, including, for example, mechanical switches, optical detection sensors, and any other sensor known in the art which would be suitable for detecting the position of a body part and/or a conductive coil relative to one another. The system may also include sensors, e.g., EMG sensors, for detecting stimulation of a target nerve, muscle, or other body tissue. The above sensors, together or alone, may ensure effective application of electromagnetic therapy via the various systems, devices and/or methods described herein.

Figure 17:
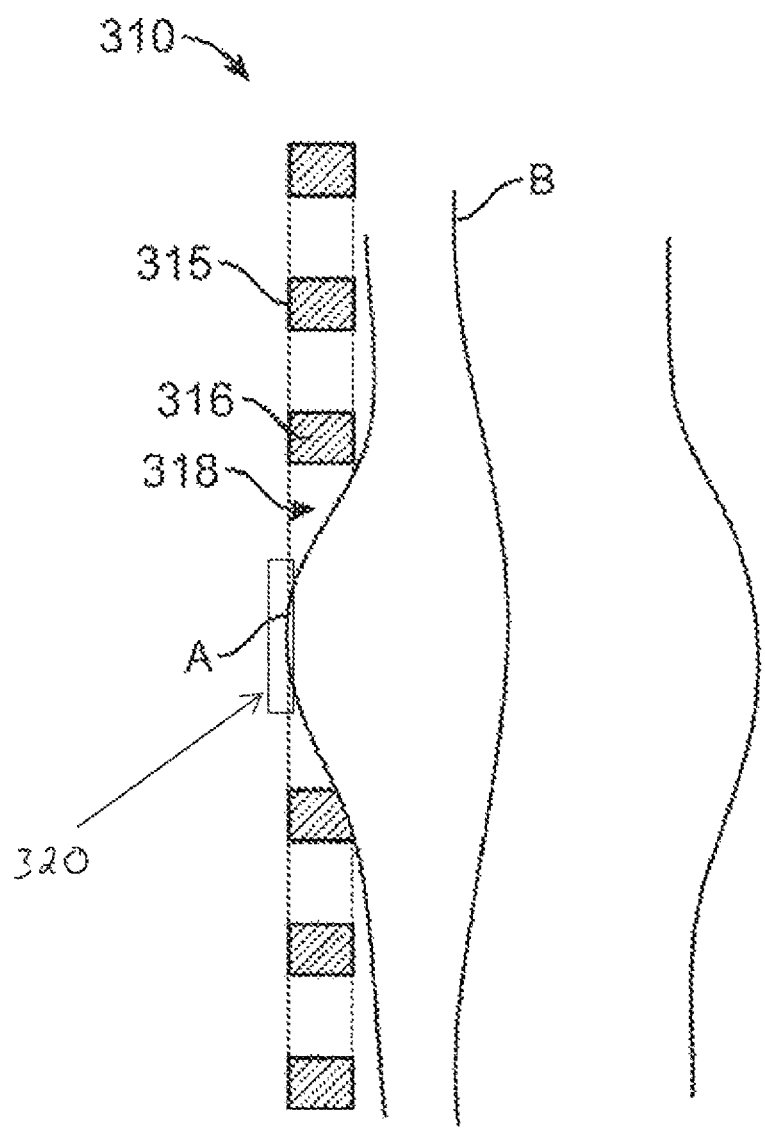
FIG. 17 shows a variation of a system including a sensor for detecting the position of a body part.

FIG. 17 shows an example of a system including a sensor 320 in the form of a mechanical switch. The mechanical switch is positioned next to or on the conductive coil 310. The mechanical switch may be thrown, moved or altered when it comes into contact with or into the proximity of a body part positioned in proximity to the coil or touching a region of the coil. In FIG. 17, the mechanical switch is shown depressed when a foot or ankle region (e.g., a malleolus) is properly positioned relative to or in proximity to the conductive coil 310. The mechanical switch or sensor may provide feedback to the system, patient, or operator regarding the positioning of the body part relative to the coil or the positioning of the coil relative to the body part prior to or during stimulation or therapy, to ensure proper positioning of the body part and/or coil such that the body part may receive effective electromagnetic stimulation. The sensor 320 may be used in any of the systems, devices or with any of the coils described or illustrated herein.

In certain variations, an energy emitting system may include a sensor 320 for detecting positioning and/or an EMG or other sensor for detecting nerve, muscle or tissue stimulation to ensure accurate or proper body part positioning in proximity to the conductive coil, and to ensure that proper stimulation is occurring in the target nerve, muscle or other body tissue.

It is also noted that in certain of the figures, various components of the system, e.g., the coil turns or central aperture, may be magnified or reduced in scale, individually or relative to one another, for illustration purposes.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become obvious to those skilled in the art and the scope of the present invention is limited only by the appended claims.

What is claimed is:

1. A method of performing electrical stimulation therapy to treat urinary incontinence in a patient, comprising:
    positioning a first portion of a patient's body relative to a microneedle electrode wherein the microneedle electrode is positioned on the skin of a patient;
    passing a current through the microneedle electrode to deliver electrical energy through the skin such that the electrical energy stimulates the posterior tibial nerve or a branch thereof;
    placing at least one sensor on a second portion of the body of the patient;
    detecting stimulation of the posterior tibial nerve or a branch thereof utilizing the at least one sensor by detecting a signal that an afferent nerve has been stimulated;
    receiving a signal from the sensor indicative of stimulation of the posterior tibial nerve or a branch thereof; and
    whereby the detection is used in modulating the current via a controller in communication with the microneedle electrode to provide an optimal dosage of therapy to treat urinary incontinence.

2. The method of claim 1 wherein passing a current comprises passing the current through a plurality of microneedles.

3. The method of claim 1 wherein modulating comprises adjusting an amplitude, frequency, direction of the electrical stimulus, or firing sequence of the microneedle electrode.

4. The method of claim 1 wherein modulating comprises adjusting a position of the microneedle electrode relative to the first portion of the patient's body to re-focus the electrical energy on the target nerve.

5. The method of claim 1 wherein the sensor is comprised of a microneedle sensor applied to a skin surface.

* * * * *